(12) United States Patent
Tamura

(10) Patent No.: US 8,313,436 B2
(45) Date of Patent: Nov. 20, 2012

(54) METHODS AND APPARATUS FOR ULTRASOUND IMAGING

(75) Inventor: Tadashi Tamura, North Haven, CT (US)

(73) Assignee: Hitachi Aloka Medical, Ltd., Tokyo (JP)

( * ) Notice: Subject to any disclaimer, the term of this patent is extended or adjusted under 35 U.S.C. 154(b) by 1486 days.

(21) Appl. No.: 11/732,462

(22) Filed: Apr. 2, 2007

(65) Prior Publication Data

US 2007/0230759 A1 Oct. 4, 2007

Related U.S. Application Data

(60) Provisional application No. 60/744,019, filed on Mar. 31, 2006, provisional application No. 60/744,020, filed on Mar. 31, 2006.

(51) Int. Cl.
*A61B 8/00* (2006.01)

(52) U.S. Cl. ........ 600/443; 600/437; 600/440; 600/447; 382/128; 382/129; 382/130; 73/631

(58) Field of Classification Search ............ 600/437, 600/440, 443, 447; 382/128–130; 73/631
See application file for complete search history.

(56) References Cited

U.S. PATENT DOCUMENTS

| | | | |
|---|---|---|---|
| 4,043,181 | A | 8/1977 | Nigam |
| 4,852,576 | A | 8/1989 | Inbar et al. |
| 5,579,768 | A | 12/1996 | Klesenski |
| 6,398,733 | B1 | 6/2002 | Simopoulos et al. |
| 2002/0002334 | A1 | 1/2002 | Okuno et al. |
| 2003/0028107 | A1 | 2/2003 | Miller et al. |
| 2006/0030775 | A1 | 2/2006 | Adams et al. |

FOREIGN PATENT DOCUMENTS

| | | |
|---|---|---|
| EP | 1 005 833 A1 | 7/2000 |
| JP | 62-117536 A | 5/1987 |
| JP | 63-302837 A | 9/1988 |
| JP | 63-240842 A | 10/1988 |
| JP | 63-302837 A | 12/1988 |
| JP | 6-54849 A | 1/1994 |
| JP | 6-54849 A | 3/1994 |
| JP | 6-114060 A | 4/1994 |
| JP | 6-114660 A | 4/1994 |
| WO | 01/80714 A1 | 11/2001 |

OTHER PUBLICATIONS

Mercier, L. et al., "A Review of Calibration Techniques for Freehand 3-D Ultrasound Systems", Ultrasound in Medicine and Biology, vol. 31, No. 4, Apr. 1, 2005, XP004849064, ISSN: 0301-5629, (pp. 339-471, 23 pages total).

"PCT International Search Report", mailed Jan. 22, 2008, for PCT/IB2007/002115, 4pgs.

"European Search Report of the European Patent Office", mailed Oct. 29, 2009 for EP 08168093.6-2220 / 2048511, 3pgs.

"European Search Report of the European Patent Office", mailed Nov. 2, 2009, for EP 08168098.5-2220 / 2048512, 2pgs.

"European Search Report of the European Patent Office", mailed Nov. 3, 2009, for EP 07789549.8-2220 / 2007285 PCT/IB2007002115, 2pgs.

"European Search Report of the European Patent Office", mailed Nov. 4, 2009, for EP 08168102.5-2220 / 2048513, 2pgs.

"Japanese Office Action and English Translation", dated Jun. 1, 2012, for Japanese Application No. 2009-502256, 5pgs.

*Primary Examiner* — Brian Casler
*Assistant Examiner* — Joseph M Santos
(74) *Attorney, Agent, or Firm* — Buckley, Maschoff & Talwalkar LLC

(57) ABSTRACT

Actual ultrasound attenuation in tissue is used to calculate gain compensation profiles which are used to create a uniform image. Axial, lateral, elevation gain profiles are used to correct the attenuation and ultrasound variation in each direction. In addition, automatic activation of the automatic gain compensation is described.

29 Claims, 18 Drawing Sheets

Fig. 2

| i \ j | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | $a_{1,1}$ | $a_{1,2}$ | $a_{1,3}$ | $a_{1,4}$ | $a_{1,5}$ | $a_{1,6}$ | $a_{1,7}$ | $a_{1,8}$ | $a_{1,9}$ | $a_{1,10}$ | $a_{1,11}$ | $a_{1,12}$ | $a_{1,13}$ | $a_{1,14}$ | $a_{1,15}$ |
| 2 | $a_{2,1}$ | $a_{2,2}$ | $a_{2,3}$ | $a_{2,4}$ | $a_{2,5}$ | $a_{2,6}$ | $a_{2,7}$ | $a_{2,8}$ | $a_{2,9}$ | $a_{2,10}$ | $a_{2,11}$ | $a_{2,12}$ | $a_{2,13}$ | $a_{2,14}$ | $a_{2,15}$ |
| 3 | $a_{3,1}$ | $a_{3,2}$ | $a_{3,3}$ | $a_{3,4}$ | $a_{3,5}$ | $a_{3,6}$ | $a_{3,7}$ | $a_{3,8}$ | $a_{3,9}$ | $a_{3,10}$ | $a_{3,11}$ | $a_{3,12}$ | $a_{3,13}$ | $a_{3,14}$ | $a_{3,15}$ |
| 4 | $a_{4,1}$ | $a_{4,2}$ | $a_{4,3}$ | $a_{4,4}$ | $a_{4,5}$ | $a_{4,6}$ | | | | | | | | | |
| 5 | $a_{5,1}$ | $a_{5,2}$ | $a_{5,3}$ | $a_{5,4}$ | $a_{5,5}$ | $a_{5,6}$ | | | | | | | | | |
| 6 | $a_{6,1}$ | $a_{6,2}$ | $a_{6,3}$ | $a_{6,4}$ | $a_{6,5}$ | $a_{6,6}$ | | | | | | | | | |
| 7 | $a_{7,1}$ | $a_{7,2}$ | $a_{7,3}$ | | | | $a_{7,7}$ | $a_{7,8}$ | $a_{7,9}$ | | | | | | |
| 8 | $a_{8,1}$ | $a_{8,2}$ | $a_{8,3}$ | | | | $a_{8,7}$ | $a_{8,8}$ | $a_{8,9}$ | | | | | | |
| 9 | $a_{9,1}$ | $a_{9,2}$ | $a_{9,3}$ | | | | $a_{9,7}$ | $a_{9,8}$ | $a_{9,9}$ | | | | | | |
| 10 | $a_{10,1}$ | $a_{10,2}$ | $a_{10,3}$ | | | | | | | $a_{10,10}$ | $a_{10,11}$ | $a_{10,12}$ | | | |
| 11 | $a_{11,1}$ | $a_{11,2}$ | $a_{11,3}$ | | | | | | | $a_{11,10}$ | $a_{11,11}$ | $a_{11,12}$ | | | |
| 12 | $a_{12,1}$ | $a_{12,2}$ | $a_{12,3}$ | | | | | | | $a_{12,10}$ | $a_{12,11}$ | $a_{12,12}$ | | | |
| 13 | $a_{13,1}$ | $a_{13,2}$ | $a_{13,3}$ | | | | | | | | | | $a_{13,13}$ | $a_{13,14}$ | $a_{13,15}$ |
| 14 | $a_{14,1}$ | $a_{14,2}$ | $a_{14,3}$ | | | | | | | | | | $a_{14,13}$ | $a_{14,14}$ | $a_{14,15}$ |
| 15 | $a_{15,1}$ | $a_{15,2}$ | $a_{15,3}$ | | | | | | | | | | $a_{15,13}$ | $a_{15,14}$ | $a_{15,15}$ |

201

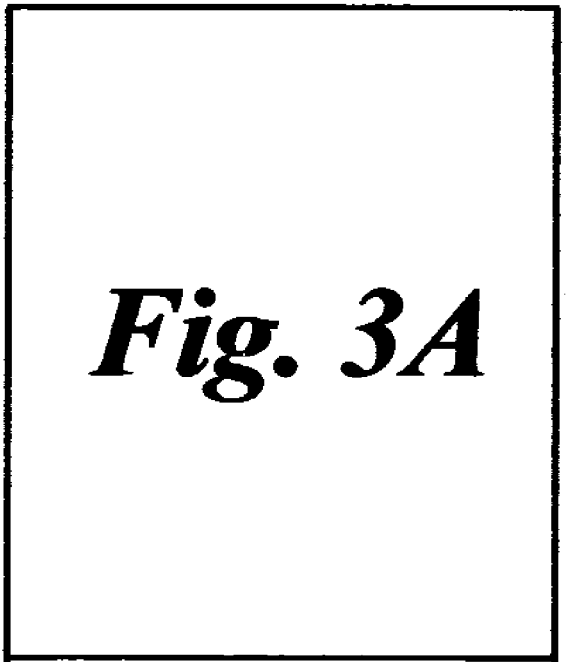
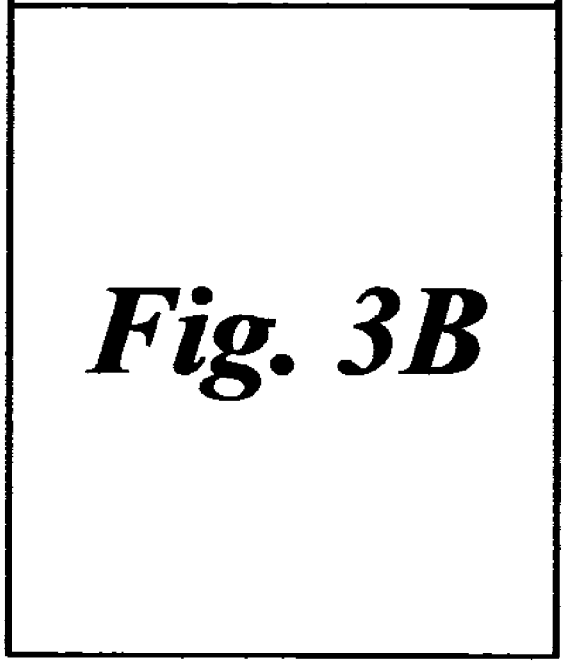
*Fig. 3*

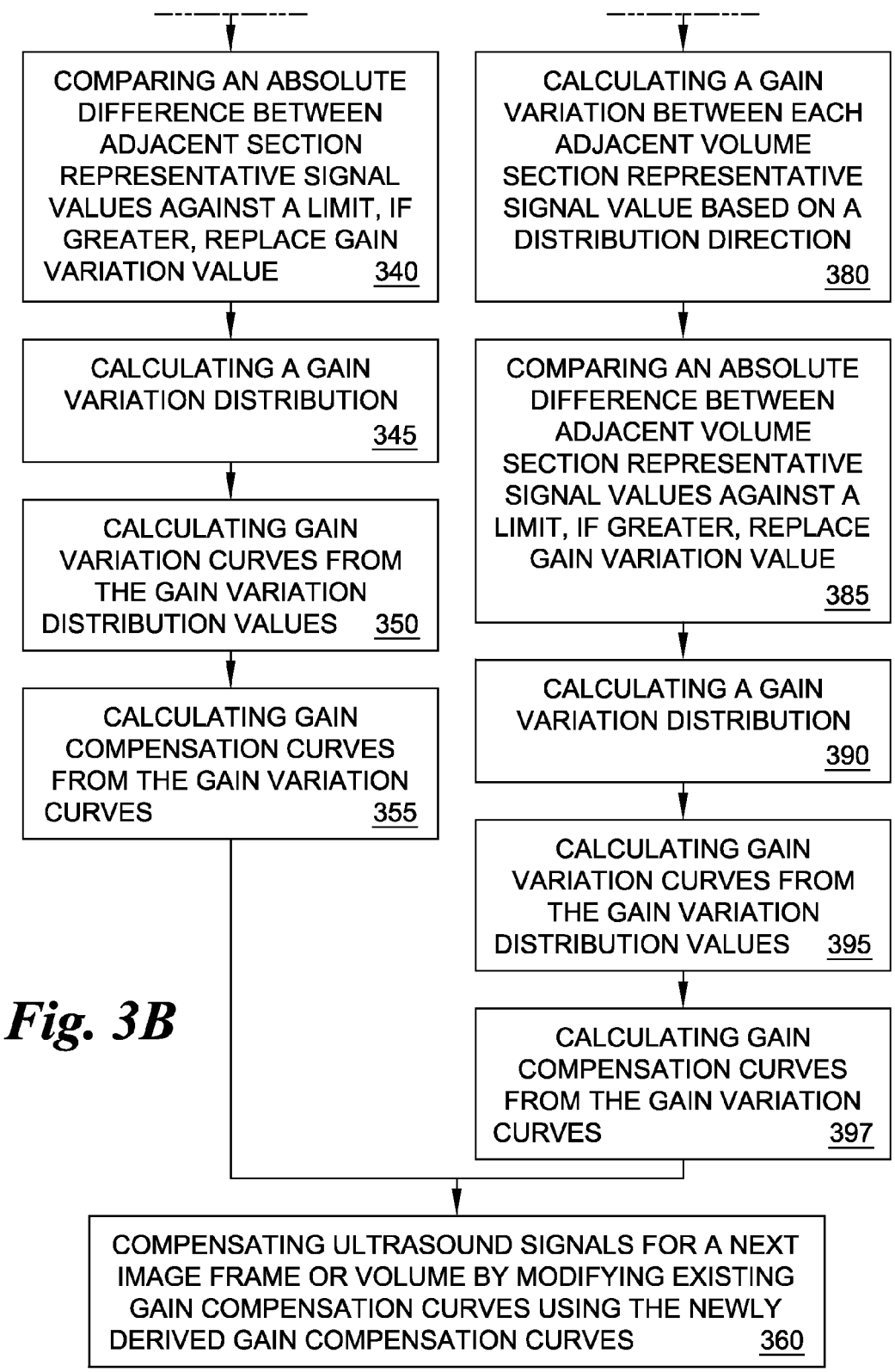

Matrix 201 (M × N), with column groups A (j=1–3), B (j=4–6), C (j=7–9), D (j=10–12), E (j=13–15):

| i \ j | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1  | $a_{1,1}$  | $a_{1,2}$  | $a_{1,3}$  | $a_{1,4}$  | $a_{1,5}$  | $a_{1,6}$  | $a_{1,7}$  | $a_{1,8}$  | $a_{1,9}$  | $a_{1,10}$  | $a_{1,11}$  | $a_{1,12}$  | $a_{1,13}$  | $a_{1,14}$  | $a_{1,15}$  |
| 2  | $a_{2,1}$  | $a_{2,2}$  | $a_{2,3}$  | $a_{2,4}$  | $a_{2,5}$  | $a_{2,6}$  | $a_{2,7}$  | $a_{2,8}$  | $a_{2,9}$  | $a_{2,10}$  | $a_{2,11}$  | $a_{2,12}$  | $a_{2,13}$  | $a_{2,14}$  | $a_{2,15}$  |
| 3  | $a_{3,1}$  | $a_{3,2}$  | $a_{3,3}$  | $a_{3,4}$  | $a_{3,5}$  | $a_{3,6}$  | $a_{3,7}$  | $a_{3,8}$  | $a_{3,9}$  | $a_{3,10}$  | $a_{3,11}$  | $a_{3,12}$  | $a_{3,13}$  | $a_{3,14}$  | $a_{3,15}$  |
| 4  | $a_{4,1}$  | $a_{4,2}$  | $a_{4,3}$  | $a_{4,4}$  | $a_{4,5}$  | $a_{4,6}$  |  |  |  |  |  |  |  |  |  |
| 5  | $a_{5,1}$  | $a_{5,2}$  | $a_{5,3}$  | $a_{5,4}$  | $a_{5,5}$  | $a_{5,6}$  |  |  |  |  |  |  |  |  |  |
| 6  | $a_{6,1}$  | $a_{6,2}$  | $a_{6,3}$  | $a_{6,4}$  | $a_{6,5}$  | $a_{6,6}$  |  |  |  |  |  |  |  |  |  |
| 7  | $a_{7,1}$  | $a_{7,2}$  | $a_{7,3}$  |  |  |  | $a_{7,7}$  | $a_{7,8}$  | $a_{7,9}$  |  |  |  |  |  |  |
| 8  | $a_{8,1}$  | $a_{8,2}$  | $a_{8,3}$  |  |  |  | $a_{8,7}$  | $a_{8,8}$  | $a_{8,9}$  |  |  |  |  |  |  |
| 9  | $a_{9,1}$  | $a_{9,2}$  | $a_{9,3}$  |  |  |  | $a_{9,7}$  | $a_{9,8}$  | $a_{9,9}$  |  |  |  |  |  |  |
| 10 | $a_{10,1}$ | $a_{10,2}$ | $a_{10,3}$ |  |  |  |  |  |  | $a_{10,10}$ | $a_{10,11}$ | $a_{10,12}$ |  |  |  |
| 11 | $a_{11,1}$ | $a_{11,2}$ | $a_{11,3}$ |  |  |  |  |  |  | $a_{11,10}$ | $a_{11,11}$ | $a_{11,12}$ |  |  |  |
| 12 | $a_{12,1}$ | $a_{12,2}$ | $a_{12,3}$ |  |  |  |  |  |  | $a_{12,10}$ | $a_{12,11}$ | $a_{12,12}$ |  |  |  |
| 13 | $a_{13,1}$ | $a_{13,2}$ | $a_{13,3}$ |  |  |  |  |  |  |  |  |  | $a_{13,13}$ | $a_{13,14}$ | $a_{13,15}$ |
| 14 | $a_{14,1}$ | $a_{14,2}$ | $a_{14,3}$ |  |  |  |  |  |  |  |  |  | $a_{14,13}$ | $a_{14,14}$ | $a_{14,15}$ |
| 15 | $a_{15,1}$ | $a_{15,2}$ | $a_{15,3}$ |  |  |  |  |  |  |  |  |  | $a_{15,13}$ | $a_{15,14}$ | $a_{15,15}$ |

| | J | I | H | G | F |
|---|---|---|---|---|---|
| | $a_{1,1}\ a_{1,2}\ a_{1,3}$<br>$a_{2,1}\ a_{2,2}\ a_{2,3}$<br>$a_{3,1}\ a_{3,2}\ a_{3,3}$ | $a_{1,4}\ a_{1,5}\ a_{1,6}$<br>$a_{2,4}\ a_{2,5}\ a_{2,6}$<br>$a_{3,4}\ a_{3,5}\ a_{3,6}$ | $a_{1,7}\ a_{1,8}\ a_{1,9}$<br>$a_{2,7}\ a_{2,8}\ a_{2,9}$<br>$a_{3,7}\ a_{3,8}\ a_{3,9}$ | $a_{1,10}\ a_{1,11}\ a_{1,12}$<br>$a_{2,10}\ a_{2,11}\ a_{2,12}$<br>$a_{3,10}\ a_{3,11}\ a_{3,12}$ | $a_{1,13}\ a_{1,14}\ a_{1,15}$<br>$a_{2,13}\ a_{2,14}\ a_{2,15}$<br>$a_{3,13}\ a_{3,14}\ a_{3,15}$ |
| | $a_{4,1}\ a_{4,2}\ a_{4,3}$<br>$a_{5,1}\ a_{5,2}\ a_{5,3}$<br>$a_{6,1}\ a_{6,2}\ a_{6,3}$ | $a_{4,4}\ a_{4,5}\ a_{4,6}$<br>$a_{5,4}\ a_{5,5}\ a_{5,6}$<br>$a_{6,4}\ a_{6,5}\ a_{6,6}$ | | | |
| | $a_{7,1}\ a_{7,2}\ a_{7,3}$<br>$a_{8,1}\ a_{8,2}\ a_{8,3}$<br>$a_{9,1}\ a_{9,2}\ a_{9,3}$ | | $a_{7,7}\ a_{7,8}\ a_{7,9}$<br>$a_{8,7}\ a_{8,8}\ a_{8,9}$<br>$a_{9,7}\ a_{9,8}\ a_{9,9}$ | | |
| | $a_{10,1}\ a_{10,2}\ a_{10,3}$<br>$a_{11,1}\ a_{11,2}\ a_{11,3}$<br>$a_{12,1}\ a_{12,2}\ a_{12,3}$ | | | $a_{10,10}\ a_{10,11}\ a_{10,12}$<br>$a_{11,10}\ a_{11,11}\ a_{11,12}$<br>$a_{12,10}\ a_{12,11}\ a_{12,12}$ | |
| | $a_{13,1}\ a_{13,2}\ a_{13,3}$<br>$a_{14,1}\ a_{14,2}\ a_{14,3}$<br>$a_{15,1}\ a_{15,2}\ a_{15,3}$ | | | | $a_{13,13}\ a_{13,14}\ a_{13,15}$<br>$a_{14,13}\ a_{14,14}\ a_{14,15}$<br>$a_{15,13}\ a_{15,14}\ a_{15,15}$ |

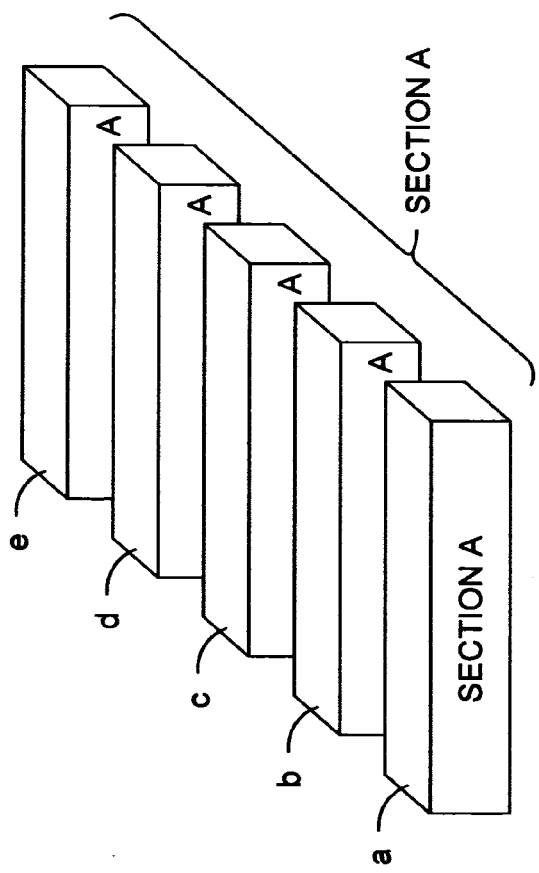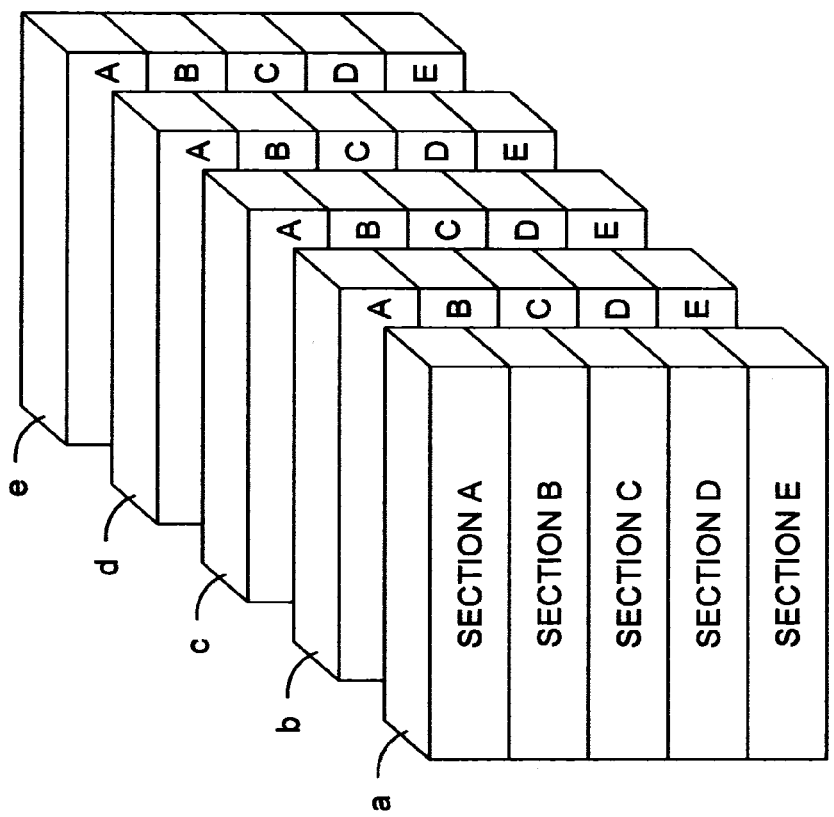
Fig. 14

METHODS AND APPARATUS FOR ULTRASOUND IMAGING

CROSS REFERENCE TO RELATED APPLICATIONS

This application claims the benefit of U.S. Provisional Application No. 60/744,019, filed on Mar. 31, 2006 and U.S. Provisional Application No. 60/744,020, filed on Mar. 31, 2006, which are incorporated herein by reference in their entirety.

BACKGROUND OF THE INVENTION

The invention relates to ultrasound imaging. More specifically, the invention relates to automatically adjusting the gain of received ultrasound signals when performing ultrasound imaging.

Ultrasound is used to image human bodies to diagnose various medical conditions of, for example, a fetus, the heart, liver, kidney and other organs. Ultrasound is transmitted by an ultrasound transducer through the skin to tissues in the human body. The ultrasound is scattered by ultrasound scatterers and is received by the ultrasound transducer. The received ultrasound is converted to an electrical signal by the ultrasound transducer and is processed to create an image of the tissues.

Ultrasound is attenuated through the human tissues at a rate of approximately 0.5 dB/MHz/cm. The intensity of the ultrasonic beam decreases as it penetrates the tissue. Therefore, two identical targets at different depths will produce different echoes with the echo produced by the closer target being larger than the other. This problem may be circumvented by using time-gain compensation (TGC) in which the gain of the received signal amplifier is increased as a function depth (time) to compensate for the loss in energy due to attenuation. Various forms of time-gain compensation have been used. In modern scanners, TGC shape may be conveniently adjusted to optimize the image or the application.

Conventional ultrasound imaging systems are usually equipped with TGC to compensate for this type of attenuation. However, most systems use either a fixed TGC or an operator adjustable TGC. If the received ultrasound signal is not compensated for, the resulting ultrasound image would be brighter at a shallow depth and darker at a larger depth resulting in a non-uniform image.

Fixed TGC uses a predetermined attenuation curve for all imaging which is not optimal since attenuation in patient's bodies varies from one patient to another. Adjustable TGC is controlled by an operator by sliding potentiometers on the control console. Typical ultrasound systems include several potentiometers for the operator to adjust to create an attenuation compensation curve that provides a uniform image. The operator needs to set the TGC potentiometers for every patient and for every location of the human body to image. If the TGC settings are set inaccurately, diagnostic quality may suffer.

Operator adjustable TGC is time consuming, and may adversely affect a patient's diagnosis. There exists a need to automatically adjust TGC using signals from the patient for each ultrasound image.

SUMMARY OF THE INVENTION

The inventor has discovered that it would be desirable to have a system and method that uses actual ultrasound tissue attenuation to calculate gain compensation profiles which are then used as compensation to correct and create a uniform image for display. Axial, lateral, elevation (for volume imaging) and combination gain profiles are used to correct gain and reduce variation across an image.

In addition to providing gain compensation, automatic activation of the gain compensation is taught. In one embodiment, motion sensors are used to detect probe movement and to activate the gain compensation system. In another embodiment, motions are detected by the ultrasound images.

One aspect of the invention provides a method for deriving gain compensating data from ultrasound image data. Methods according to this aspect of the invention comprise receiving ultrasound image data corresponding to an image scan, assembling an image frame from the ultrasound image data, the image frame having columns and rows of image data values where columns represent lateral position and rows represent axial position, partitioning the image data frame into a plurality of sections, calculating a representative signal value for each section, calculating gain variations between adjacent section representative signal values, calculating a gain variation distribution from the gain variations between sections, calculating a gain variation curve from the gain variation distribution, and calculating a gain compensating curve from the gain variation curve, wherein a compensating gain value corresponds with a position.

Another aspect is wherein the ultrasound imaging data comprises RF data, IF data, baseband signal data, detected baseband signal data, log-compressed detected baseband signal data, line data or image data.

Another aspect of the invention provides a method for deriving gain compensating data for an ultrasound image volume. Methods according to this aspect of the invention comprise receiving ultrasound image data corresponding to a plurality of consecutive image scans, assembling an image volume from the plurality of image scans, the image volume having three dimensions of image data values where columns represent lateral position, rows represent axial position, and frames represent elevation position, partitioning the volume into a plurality of volume sections, calculating a representative signal value for each volume section, calculating a gain variation between adjacent volume section representative signal values, calculating a gain variation distribution from the gain variations between volume sections, calculating a gain variation curve from the gain variation distribution, and calculating a gain compensating curve from the gain variation curve, wherein a compensating gain value corresponds with a position.

Another aspect of the invention provides a method for activating an automatic gain compensation data system for ultrasound systems. Methods according to this aspect comprise receiving ultrasound image data corresponding to consecutive image scans, and performing a correlation analysis between image data for each received scan, wherein the correlation analysis returns a value representative of probe movement, and if a detected change is greater than a predetermined value, the probe may be considered moved initiating new gain compensation calculations.

Another aspect is wherein the correlation analyses are correlation, sum of absolute differences D (SAD), sum of square differences (SSD), sum of cubic differences, and sum of powered differences $D^q$.

Another aspect of the invention provides a method for activating an automatic gain compensation data system for ultrasound systems. Methods according to this aspect comprise receiving ultrasound image data corresponding to consecutive image scans, and observing gain variation changes between axial, lateral or elevation sections, wherein if a detected change is greater than a predetermined value, the probe may be considered moved initiating new gain compensation calculation.

Another aspect of the invention provides a method for activating an automatic gain compensation data system for ultrasound systems. Methods according to this aspect comprise receiving ultrasound image data corresponding to consecutive image scans, and detecting motions by correlation, SAD or SSD, SCD or sum of powered differences wherein if a detected change is greater than a predetermined value, the probe may be considered moved initiating new gain compensation calculation to compensate for new gain changes.

Another aspect of the invention provides a method for activating an automatic gain compensation data system for ultrasound systems. Methods according to this aspect comprise detecting motion using a motion sensor attached to an ultrasound probe, wherein if motion is greater than a predetermined value, the probe is considered moved, initiating new gain compensation calculations.

Another aspect of the invention provides a method for controlling the gains of TGC amplifiers, and axial, lateral and elevation variable gain amplifiers of an ultrasound system while acquiring ultrasound image data. Methods according to this aspect comprise receiving axial, lateral and elevation gain compensating data from an ultrasound image, receiving ultrasound signals from the ultrasound system, calculating an overall gain value from the received ultrasound signals, calculating TGC, axial, lateral and elevation amplifier gain data from previous axial, lateral and elevation combination gain data, and received axial, lateral and elevation gain compensating data, and the overall gain data; and distributing the TGC, axial, lateral and elevation amplifier gain data to the respective amplifiers.

Another aspect of the invention is an automatic gain compensation system for deriving gain compensating data for ultrasound systems having amplifiers configured to adjust a received signal's gain while acquiring ultrasound image data. Systems according to this aspect comprise an automatic gain processor configured for receiving ultrasound image data corresponding to an image scan, assembling an image frame from the ultrasound image data, the image frame having columns and rows of image data values where columns represent lateral position and rows represent axial position, partitioning the image data frame into a plurality of sections, calculating a representative signal value for each section, calculating gain variations between adjacent section representative signal values, calculating a gain variation distribution from the gain variations between sections, calculating a gain variation curve from the gain variation distribution, and calculating a gain compensating curve from the gain variation curve, wherein a compensating gain value corresponds with a position.

Another aspect of the invention is an automatic gain compensation system for deriving gain compensating data for ultrasound systems having amplifiers configured to adjust a received signal's gain while acquiring ultrasound image data. Systems according to this aspect comprise an automatic gain processor configured for receiving ultrasound image data corresponding to a plurality of consecutive image scans, assembling an image volume from the plurality of image scans, the image volume having three dimensions of image data values where columns represent lateral position, rows represent axial position, and frames represent elevation position, partitioning the volume into a plurality of volume sections, calculating a representative signal value for each volume section, calculating a gain variation between adjacent volume section representative signal values, calculating a gain variation distribution from the gain variations between volume sections, calculating a gain variation curve from the gain variation distribution, and calculating a gain compensating curve from the gain variation curve, wherein a compensating gain value corresponds with a position.

Another aspect of the invention is a system for activating an automatic gain compensation data system for ultrasound systems. Systems according to this aspect comprise means for receiving ultrasound image data corresponding to consecutive image scans, and means for performing a correlation analysis between image data for each received scan, wherein the correlation analysis returns a value representative of probe movement, and if a detected change is greater than a predetermined value, the probe may be considered moved initiating new gain compensation calculations.

Another aspect of the system is wherein the correlation analyses are correlation, sum of absolute differences D (SAD), sum of square differences (SSD), sum of cubic differences, and sum of powered differences $D^q$.

Another aspect of the invention is a system for activating an automatic gain compensation data system for ultrasound systems. Systems according to this aspect comprise means for receiving ultrasound image data corresponding to consecutive image scans, and means for observing gain variation changes between axial, lateral or elevation sections, wherein if a detected change is greater than a predetermined value, the probe may be considered moved initiating new gain compensation calculation.

Another aspect of the invention is a system for activating an automatic gain compensation data system for ultrasound systems. Systems according to this aspect comprise means for receiving ultrasound image data corresponding to consecutive image scans, and means for detecting motions by correlation, SAD or SSD, SCD or sum of powered differences wherein if a detected change is greater than a predetermined value, the probe may be considered moved initiating new gain compensation calculation to compensate for new gain changes.

Another aspect of the invention is a system for activating an automatic gain compensation data system for ultrasound systems. Systems according to this aspect comprise means for detecting motion using a motion sensor attached to an ultrasound probe, wherein if motion is greater than a predetermined value, the probe is considered moved, initiating new gain compensation calculations.

Another aspect of the system is wherein the motion sensor is a velocimeter, accelerometer, gyroscope, motion tracking device, and a position sensor.

Another aspect of the invention is a system for controlling the gains of TGC amplifiers, and axial, lateral and elevation variable gain amplifiers of an ultrasound system while acquiring ultrasound image data. Systems according to this aspect comprise a processor configured for receiving axial, lateral and elevation gain compensating data from an ultrasound image, receiving ultrasound signals from the ultrasound system, calculating an overall gain value from the received ultrasound signals, calculating TGC, axial, lateral and elevation amplifier gain data from previous axial, lateral and elevation combination gain data, and received axial, lateral and elevation gain compensating data, and the overall gain data, and distributing the TGC, axial, lateral and elevation amplifier gain data to the respective amplifiers.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 2 is an exemplary image data frame.

FIG. 3 is an exemplary method.

FIG. 3B is a second portion of the FIG. 3 exemplary method.

FIG. 4 is an exemplary axial sectioning of the image data frame shown in FIG. 2.

FIG. 8 is an exemplary lateral sectioning of the image data frame shown in FIG. 2.

FIG. 14 is an exemplary axial sectioning of a five image data frame volume.

DETAILED DESCRIPTION

Figure 1:
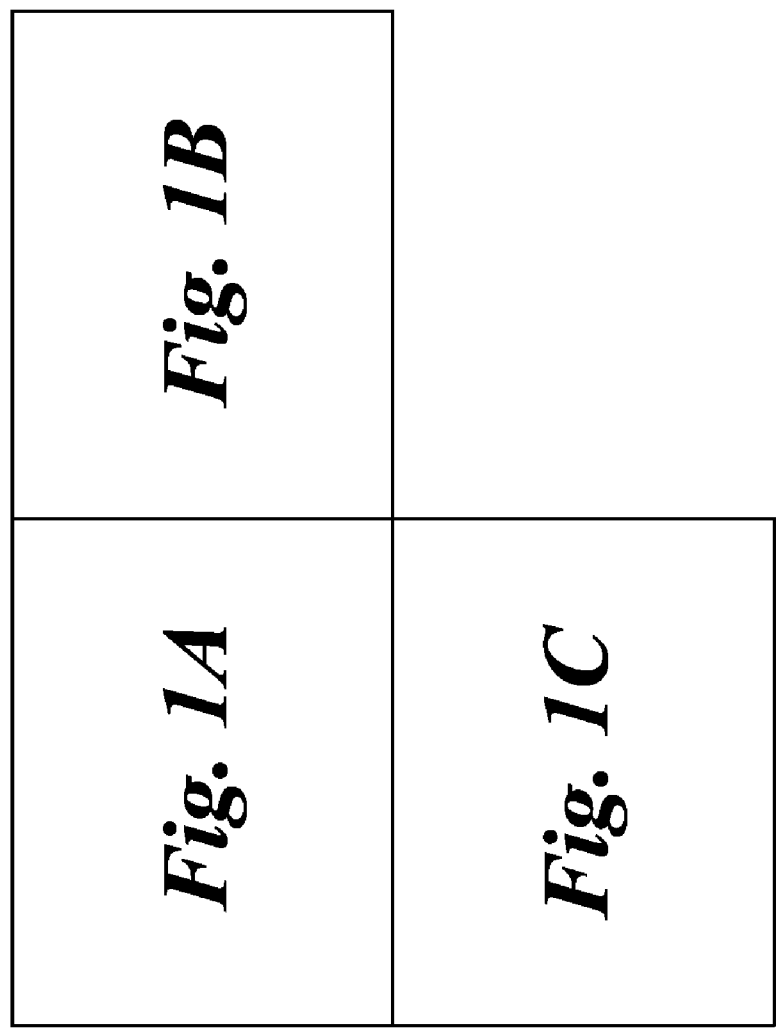
FIG. 1 is an exemplary embodiment of a typical ultrasound system with the automatic gain compensation system.
Figure 1A:
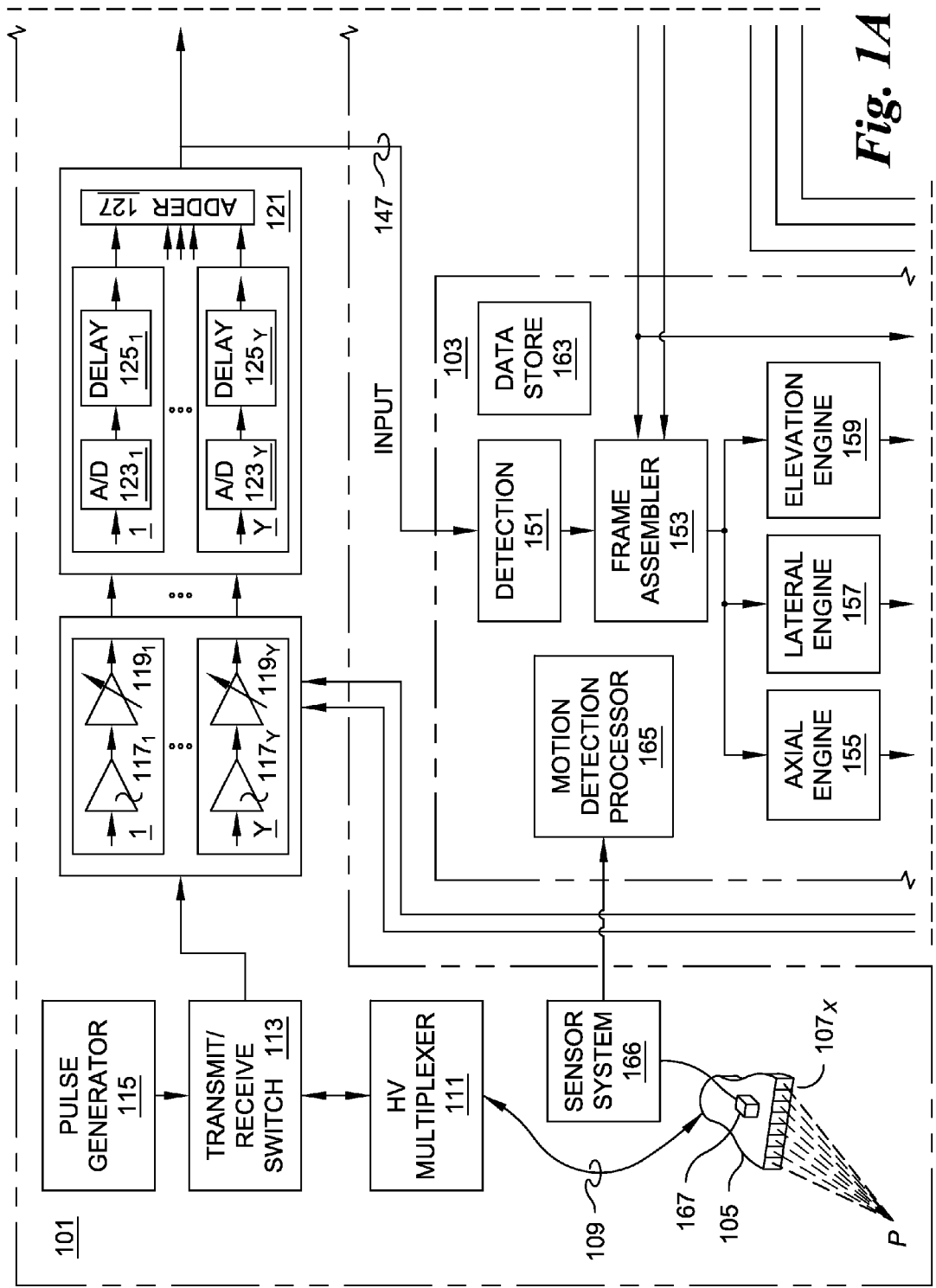
FIG. 1A illustrates an upper-left portion of the FIG. 1 exemplary embodiment.
Figure 1B:
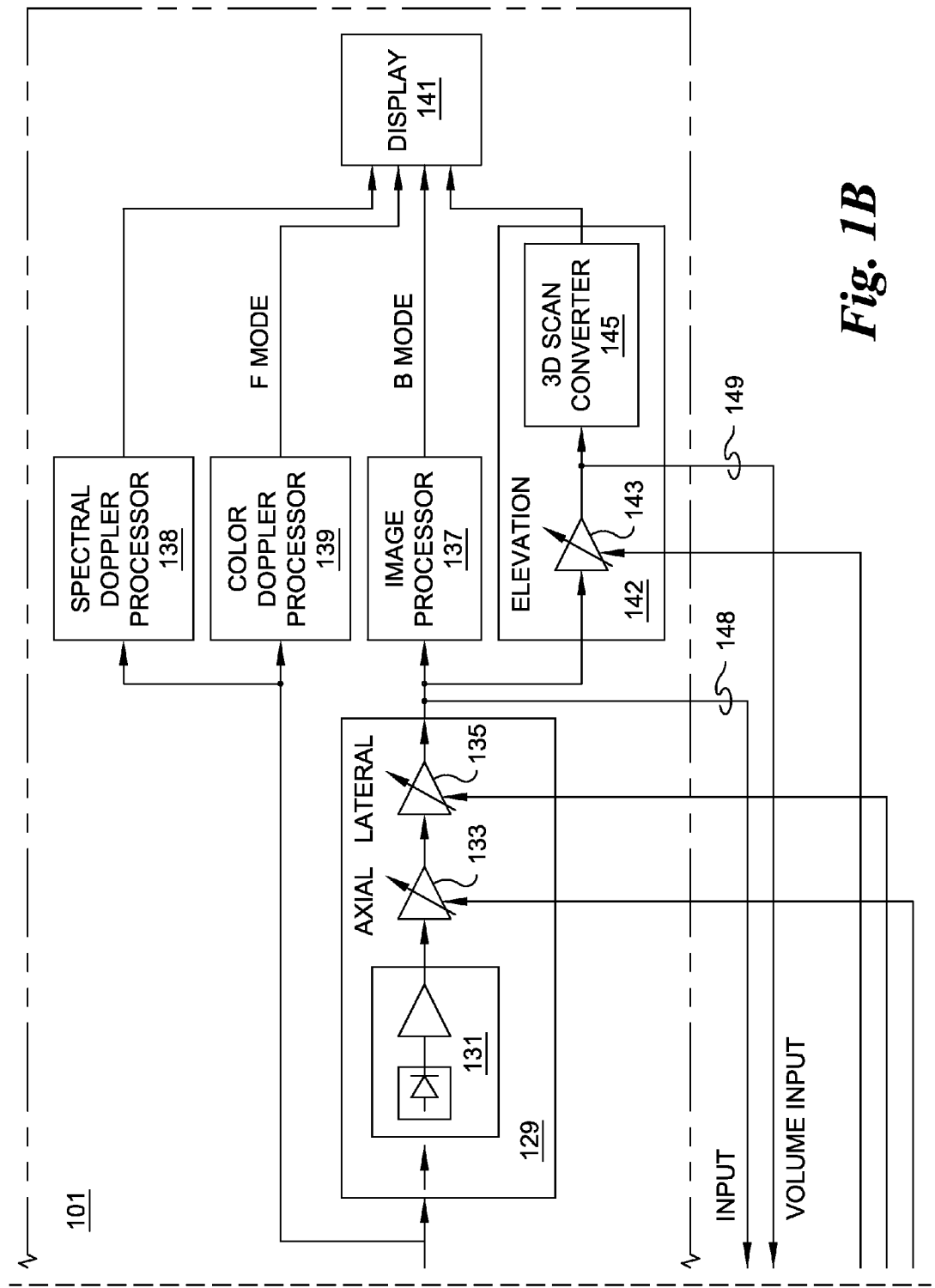
FIG. 1B illustrates an upper-right portion of the FIG. 1 exemplary embodiment.
Figure 1C:
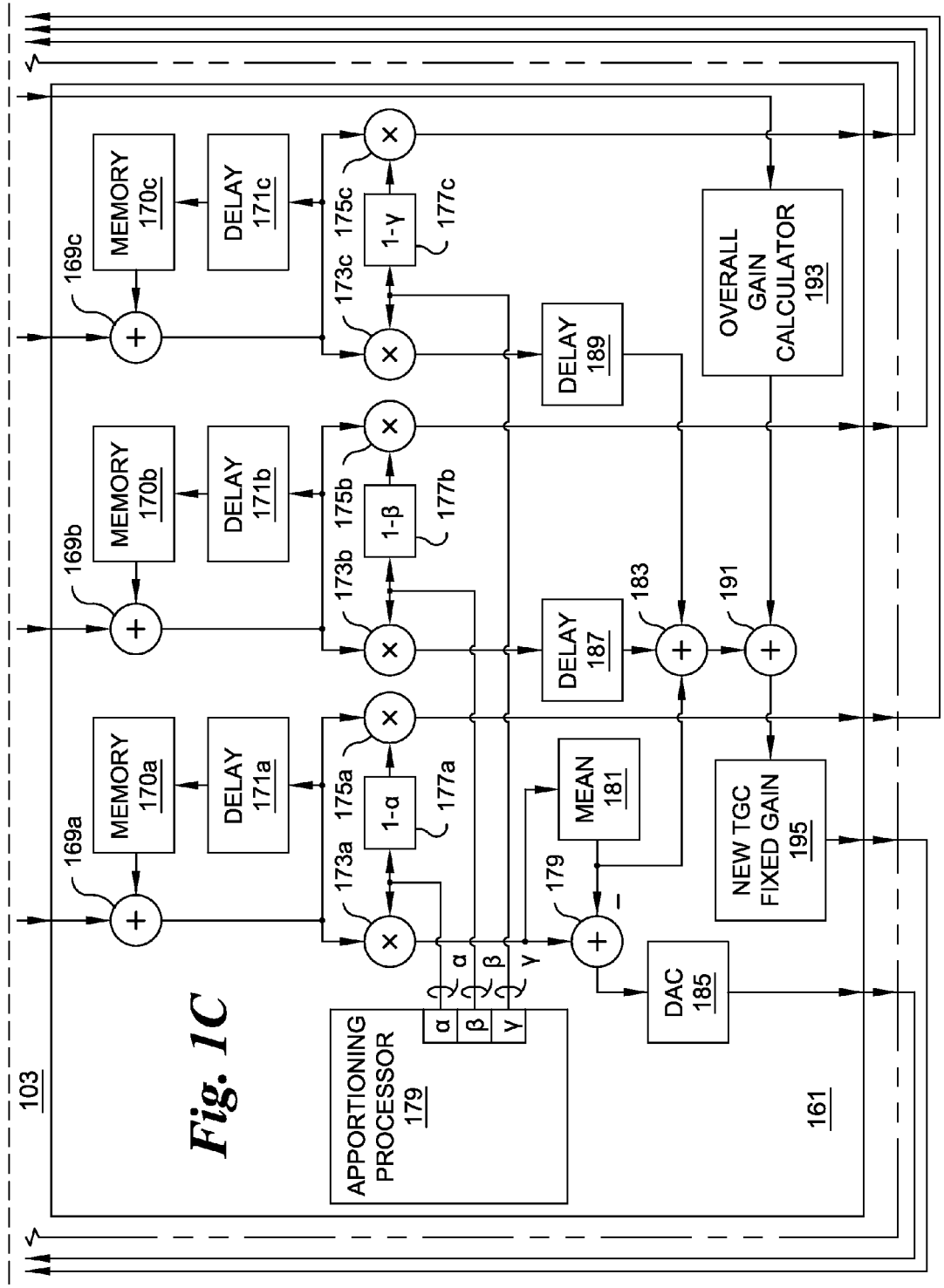
FIG. 1C illustrates a lower left portion of the FIG. 1 exemplary embodiment.

Embodiments of the invention will be described with reference to the accompanying drawing figures wherein like numbers represent like elements throughout. Before embodiments of the invention are explained in detail, it is to be understood that the invention is not limited in its application to the details of the examples set forth in the following description or illustrated in the figures. The invention is capable of other embodiments and of being practiced or carried out in a variety of applications and in various ways. Also, it is to be understood that the phraseology and terminology used herein if for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

It should be noted that the invention is not limited to any particular software language described or that is implied in the figures. One of ordinary skill in the art will understand that a variety of alternative software languages may be used for implementation of the invention. It should also be understood that some of the components and items are illustrated and described as if they were hardware elements, as is common practice within the art. However, one of ordinary skill in the art, and based on a reading of this detailed description, would understand that, in at least one embodiment, components in the method and system may be implemented in software or hardware.

Embodiments of the invention provide methods, systems, and a computer-usable medium storing computer-readable instructions that efficiently process ultrasound image data into axial, lateral and elevation gain compensation curves for real-time diagnostic imaging applications. The invention efficiently analyzes data from one ultrasound image data frame, or for volumes, a plurality of image data frames, and derives gain compensation profiles or curves for each image dimension. The invention is a modular framework and may be deployed as hardware resident in an enclosure having an onboard power supply, or as software as an application program tangibly embodied on a program storage device for executing with a processor. The application code for execution may reside on a plurality of different types of computer readable media.

By way of background, ultrasonography (sonography) uses a probe containing one or more acoustic transducers to send pulses of sound into a material. A sound wave is typically produced by creating short, strong pulses of sound from an array of piezoelectric transducers encased in a probe. The frequencies used for medical imaging are generally in the range of from 1 to 20 MHz which are medium to high ultrasound frequencies and may produce a single, focused sound wave from the sum of all the individual pulses emitted by the transducer. Higher frequencies have a correspondingly lower wavelength and yield higher spatial resolution images. Sonography may use systems employing a fundamantal frequency as well as systems employing harmonics of the fundamental frequency.

Whenever the sound wave encounters a material with a different acoustical impedance, part of the sound wave is reflected, which the transducer detects as an echo. The return sound wave vibrates the transducer's elements and turns that vibration into electrical pulses that are sent from the probe to a processor where they are processed and transformed into an image. The time it takes for the echo to travel back to the probe is measured and used to calculate the depth of the tissue interface causing the echo.

To generate a two-dimensional image, the ultrasound beam is swept electronically using an array transducer (e.g. phased array, linear array, convex array and others). Alternately, a single element transducer or an annular array transducer can be used and mechanically scanned to create a two-dimensional image. The received RF data is further processed and used to construct an ultrasound image. An array transducer may be equiped with a mechanical-scan device that allows the transducer to be mechanically swept in addition to the array's electronic scanning such that volume data for three-dimensional imaging may be obtained.

The ultrasound system can determine the location of organ or target tissue based on ultrasound measured travel-time, provided a fixed sound speed of approximately 1540 m/s. Large echo signals would appear bright in the image while small echo signals would appear dark.

The received data is referred to as RF data values and its representation is similar to that of a matrix. For example, with i identifying axial rows and j identifying lateral columns where i=1, 2, 3, ..., M and j=1, 2, 3, ..., N. The RF data values $a_{i,j}$ are typically bipolar (±) multi-bit values. For example, a 2048×128 RF data frame may have 262,144 image data values $a_{i,j}$.

Shown in FIG. 1 are a typical ultrasound system 101 and an exemplary embodiment of the automatic gain compensation system 103. The automatic gain compensation system 103 may be employed with any ultrasound imaging system 101.

The ultrasound system 101 comprises a probe 105 having a transducer array comprising a plurality of elements $107_x$-$107_X$, where X is the number of rectangular elements that may be arranged in a line as a linear array, the number of square elements arranged in rows and columns as a two-dimensional array, or ring-shaped elements arranged concentrically as an annular array. The probe 105 is coupled to a microcoaxial cable 109 typically having X coaxial cables.

The cable 109 may be coupled to a high voltage multiplexer 111 to reduce hardware complexity, or may be coupled directly to a transmit/receive switch 113 which blocks the high transmit voltage pulses 115. The transmit/receive switch 113 outputs are coupled to a plurality of channels Y. Each channel may comprise a low noise preamplifier $117_y$, coupled to a time-gain compensation (TGC) amplifier $119_y$. Each TGC amplifier $119_y$ comprises a variable gain amplifier section and a programmable gain amplifier section which may produce a fixed gain for an axial direction.

The outputs of all channels Y ($119_y$-$119_y$) are coupled to a digital beamformer 121 which steers and focuses the plurality of individual channel y outputs into one beam. The beamformer 121 may comprise a plurality of A/D converters $123_y$-$123_Y$ each coupled to a variable delay $125_y$-$125_Y$ such as a FIFO and/or a phase rotator. The delayed channels are coupled to a digital adder 127 and output.

The output from the beamformer 121 is coupled to a cascaded amplifier section 129 that may comprise a detection and logarithmic amplifier 131 to compress the dynamic range before downstream gain and image processing. The detection and log amplifier 131 is coupled to a variable gain axial amplifier 133, which is coupled to a variable gain lateral amplifier 135. The amplifier section 129 is coupled to an image processor 137 for B mode imaging processing, to a color Doppler processor 139 for flow mode processing, to a spectral Doppler processor 138, and to a volume processor 142 comprising a variable gain elevation amplifier 143 and a three-dimensional scan converter 145. The outputs of the processors 137, 139 and converter 145 are coupled to a display 141. The processors 137, 139 and converter 145 store image frame values and assembled image frames.

As described above, an array probe 105 may contain from 32 to 300 transducer elements $107_x$ that may be focused and steered by properly delaying the signals going to the elements for transmission, and delaying ($125_y$) the signals after reception. The purpose of focusing is to improve lateral image resolution. A pulse 115 exciting the center element of the probe 105 is delayed by a time period relative to the pulses 115 exciting the elements at the perimeter of the probe 105, so that all transducer pulses $107_x$ arrive at a focus point P in the tissue simultaneously. During reception, the transducer elements $107_x$ may be continuously focused from shallow to deep areas.

Upon reception, ultrasound signals from the plurality of probe 105 transducer elements $107_x$ are focused and steered into one beam by the beamformer 121. The process is repeated, forming another beam adjacent to the previous beam until an end position is reached. From the 32 to 300 transducer elements $107_x$, 50 to 500 lateral beams may be produced via focusing and steering, with each beam comprising from about 100 to 1,000 image data values $a_{i,j}$ in the axial direction. The plurality of beams and image data values form one two-dimensional image data frame after scan conversion.

The exemplary ultrasound system 101 uses a digital beamformer 121. However, in other embodiments, an analog beamformer which uses analog delay components, may be used. Furthermore, an ultrasound system using a mechanical-scan, single element transducer 107, which uses an acoustic lens for focusing may be also used.

The automatic gain compensation system 103 receives as inputs image data 147 output from the beamformer 121, image data 148 output from the variable gain lateral amplifier 129 and image data 149 output from the variable gain elevation amplifier 143. The automatic gain compensation system 103 outputs control signals to the variable gain TGC amplifiers $119_y$, the variable gain axial amplifier 133, the variable gain lateral amplifier 135 and the variable gain elevation amplifier 143.

The automatic gain compensation system 103 may comprise a detector/logarithmic amplifier 151 coupled to a frame assembler 153 for compressing and processing RF signals output from the beamformer 121. The image data 148, 149 output from the variable gain lateral amplifier 135 and variable gain elevation amplifier 143 is coupled to the frame assembler 153. Image data may comprise amplitude (p), power ($p^2$), ($p^3$), ($p^4$), $p^q$, or any signal derived from amplitude or power, where q is a real number. In one embodiment, coupled to the frame assembler 153 is an axial gain variation engine 155, a lateral gain variation engine 157, and an elevation gain variation engine 159 configured for parallel processing. Alternatively, the axial, lateral and elevation engine functionality may be combined into one engine and serially processed. The three engines 155, 157, 159 output compensation data coupled to a director 161 which may apportion the compensation data output to the variable gain TGC amplifiers $119_y$, the variable gain axial amplifier 133, the variable gain lateral amplifier 135 and the variable gain elevation amplifier 143 to compensate for signal gain variations in one or more directions.

To perform gain compensation data calculations, the automatic gain compensation system 103 may be initiated by a user, by motion detection. For motion detection, a processor 165 is coupled to the detector 151 and frame assembler 153. The motion processor 165 may perform correlation using the RF signal output from the beamformer 121, or using baseband, line data or image data from the frame assembler 153 to sense when the ultrasound probe 105 is moved from one position to another. Correlation may be performed between frames or before and after movement.

$$\rho(S^1, S^2, X, Y) = \frac{\sum_{x=1}^{m}\sum_{y=1}^{n}(S^1_{x,y} - \overline{S^1})(S^2_{x+X,y+Y} - \overline{S^2})}{\sqrt{\sum_{x=1}^{m}\sum_{y=1}^{n}(S^1_{x,y} - \overline{S^1})^2 \cdot \sum_{x=1}^{m}\sum_{y=1}^{n}(S^2_{x+X,y+Y} - \overline{S^2})^2}} \quad (1)$$

Alternatively, the processor 165 may use the sum of absolute differences (SAD)

$$SAD(S^1, S^2, X, Y) = \sum_{x=1}^{m}\sum_{y=1}^{n}|S^1_{x,y} - S^2_{x+X,y+Y}|, \quad (2)$$

or sum of square differences (SSD)

$$SSD(S^1, S^2, X, Y) = \sum_{x=1}^{m} \sum_{y=1}^{n} (S^1_{x,y} - S^2_{x+X,y+Y})^2, \quad (3)$$

or the sum of cubic differences (SCD)

$$SCD(S^1, S^2, X, Y) = \sum_{x=1}^{m} \sum_{y=1}^{n} |S^1_{x,y} - S^2_{x+X,y+Y}|^3. \quad (4)$$

Moreover, the sum of powered differences (SPD)

$$SPD(S^1, S^2, X, Y) = \sum_{x=1}^{m} \sum_{y=1}^{n} |S^1_{x,y} - S^2_{x+X,y+Y}|^q \quad (5)$$

may be used, where $S^1_{x,y}$ is an ultrasound signal at x,y of a first frame, $S^2_{x+X,y+Y}$ is an ultrasound signal at x+X,y+Y of a second frame, q is a real number, m and n define a correlation window size, and $\overline{S^1}$ and $\overline{S^2}$ are mean in the windows of the first and second frames. In one embodiment, these equations may be used to find the minimum value to track ultrasound signals to obtain a motion (X,Y). For the case of correlation, a search for the maximum value correlation is performed to obtain a motion. If the motion is greater than a predetermined value, the probe is considered moved, initiating the automatic gain compensation system 103. Alternatively, these equations with X=0, Y=0 may be used to calculate overall correlation between two frames to show the quality of a still image. If these values except correlation (1) are greater than a preset value, the probe is considered moved, initiating the automatic gain compensation system 103. In case of correlation in (1), if the correlation is smaller than a preset value, the probe is considered moved, initiating the automatic gain compensation system 103.

Initiation of gain compensation of the TGC, axial, lateral and elevation amplifiers 119$_y$, 133, 135, 143 may be performed when gain compensation data changes. Gain variation data from the axial 155, lateral 157, or elevation 159 engines may be monitored by the motion processor 165. A first tissue region as compared to another may significantly change ultrasound signals indicating probe movement whereby new gain variation data is needed. If the detected motion is more than a predefined value, the probe 105 may be considered moved, initiating gain compensation including setting the amplifiers' gains using new gain compensation curves. In an alternate embodiment, a gain variation and compensation calculation is initiated only when motion is detected. The new gain compensation modifies any previous gain applied to the amplifiers.

Motion may also be detected by using a motion sensor 167 attached to the probe 105. Motion sensors such as a velocimeter, accelerometer, gyroscope or motion tracking device or position sensor such as an Ascension Technology Corporation flock of birds sensor may be coupled to the motion detection processor 165 through the motion sensor system 166. If motion, velocity or acceleration is greater than a predetermined value, the probe is considered moved, and a gain compensation calculation is performed. In another embodiment, the automatic gain compensation system 103 may be activated periodically, for example, at predetermined time intervals.

The axial 155, lateral 157 and elevation 159 engines may be DSPs, ASICs (application specific integrated circuit), FPGAs (field programmable gate array), general purpose processors, memories or discreet devices such as adders, multipliers, dividers and other devices, or a combination of the component types. The automatic gain compensation system 103 may be comprised of DSPs, ASICs, FPGAs, general purpose processors or discreet devices, or a combination of the component types. The automatic gain compensation system 103 may accept line data, baseband data, or RF signal data as image data input. In an alternative embodiment, the system 103 may also use ultrasound image data output from the processors 137 such as regular ultrasound B-mode (grayscale) line data. The line data may be used to calculate gain compensation curves. If beamformed RF data 147 is used, the system 103 performs detection 151 to obtain the amplitude of the signal. Detection 151 may be performed using quadrature detection, mixers (multipliers), lowpass filtering, a Hilbert transform, or amplitude detection.

The automatic gain compensation system 103 may perform several different analyses of the image data values. The analyses may include, for one image frame, an axial gain analysis and/or a lateral gain analysis. One or both gain compensations may be applied to data signals received from subsequent image scans. For three-dimension or volume imaging, a predefined series of image frames are required. Volume imaging may include an elevation volume gain analysis determining gain between frames, or groups of frames, an axial volume analysis and/or a lateral volume analysis. A combination of any of the three analyses may be applied to a next received volume.

Software containing the gain compensation method of the invention may be loaded into a data store 163 and executed in the different engines 155, 157, 159 to perform gain variation and gain compensation curves computations. Since a gain variation curve is calculated based on actual patient ultrasound data, the channel TGC amplifiers 119$_y$ typically perform best for a subsequent image scan after compensation, offering the best dynamic range and signal to noise ratio (SNR).

To derive an axial or lateral gain compensation curve, the frame image data values $a_{i,j}$ must be partitioned in accordance with the desired analysis.

Figure 3A:
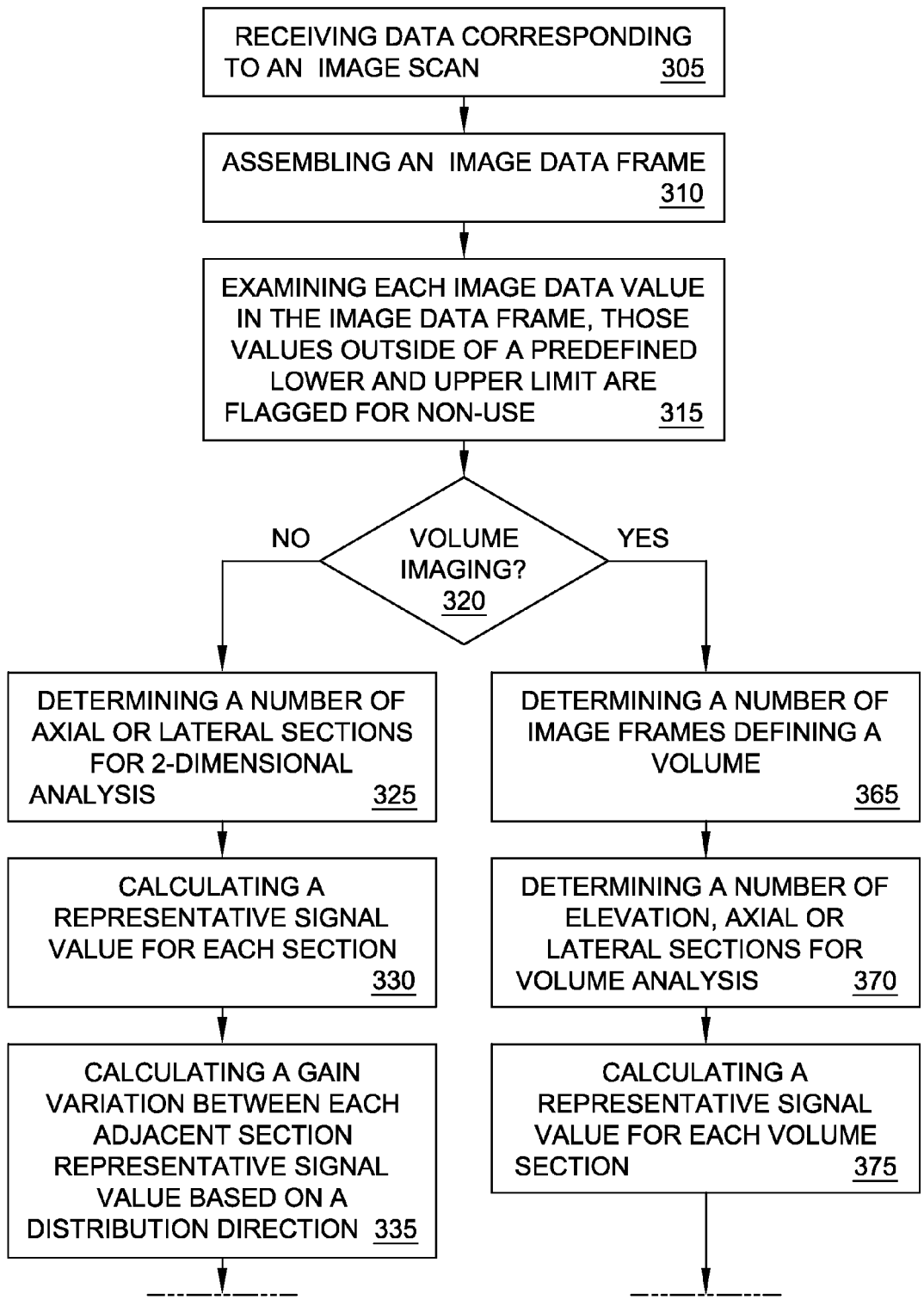
FIG. 3A is a first portion of the FIG. 3 exemplary method.

Shown in FIG. 2 is an exemplary image data frame 201. FIG. 3 shows the method of the invention. For simplicity, the exemplary frame is assembled from 15 beams N=15, each having 15 image values M=15, totaling 225 image values $a_{i,j}$ (steps 305, 310). Each image data value $a_{i,j}$ may be a multibit value comprising, for example, 8 bits representing 255 image levels ($2^n-1$, where n=8).

Lower and upper limits $limit_{lower}$, $limit_{upper}$ are determined and may be applied to each image data $a_{i,j}$ value in the frame. Ultrasound signals returned from blood or other fluids exhibits lower signal amplitudes than those from healthy soft tissue. Therefore, signals having an amplitude less than the low limit $a_{i,j} \leq limit_{lower}$ are identified and flagged. In contrast, ultrasound returned from organ borders or bone exhibits extremely high signal amplitudes. Signals having an amplitude greater than the upper limit $a_{i,j} \geq limit_{upper}$ are identified and flagged for non-use since these signals do not represent soft tissue. The flagged image data values are not considered valid $limit_{lower} < a_{i,j} < limit_{upper}$ and are not included in gain variation curve calculations (step 315). Therefore, in the exemplary image data frame 201, there may be less than 255 valid image values.

The method performs a partitioning of an image data frame into sections depending upon whether a two-dimensional axial and/or lateral analysis is desired, or if a three-dimensional elevation, axial and/or lateral analysis is desired.

FIG. 4 shows an axial partitioning of the exemplary image data frame of FIG. 2. For simplicity, the frame is partitioned into five equal axial sections (AS) A, B, C, D, and E, each axial section having three unique rows for a two-dimensional analysis (step 325). Each section may contain up to 45 valid image data values $a_{i,j}$. However, the frame may be partitioned into any number of sections having the same or different number of valid image data values per section. In other variants, some sections may overlap with other sections sharing valid image data values $a_{i,j}$. Since not all of the valid image data values may be used, sections may be represented as any separate shape such as separate or intersecting circles or ellipses. The valid image data values $a_{i,j}$ in a defined axial section are used.

The axial engine 155 computes a representative signal value (I) for each defined axial section ASA, ASB, ASC, ASD, and ASE using the valid image data values $a_{i,j}$ within each section. Section signal analysis may be performed using methods such as histograms, percentile value, mean, median, mode, and others. For this example, histograms and a percentile value are used to derive section representative signal values.

For each histogram, the number of valid image data $a_{i,j}$ values $\text{limit}_{lower} < a_{i,j} < \text{limit}_{upper}$ in a section are mapped corresponding to their value. A histogram is simply a mapping that counts the number of observations or occurrences, image data values $a_{i,j}$ in this case, that fall into various values (or disjoint categories) known as bins.

If the image data values $a_{i,j}$ are 8 bit binary numbers, each value may take on a number between 0 and 255. The histogram forms an intensity distribution. A percentile of the resulting histogram distribution is taken, which then becomes a representative signal value for that section. The histogram may yield a percentile value, for example, 70%. The percentile value of 70% is a threshold value below which 70% percent of the image data values $a_{i,j}$ used for that section fall in. The 50% percentile is the median.

The representative signal values calculated for each axial section (step 330) ASA, ASB, ASC, ASD and ASE are compared with adjacent axial section representative signal values. The axial section representative signal values for ASA, ASB, ASC, ASD and ASE may be converted to decibels (dB) if not in decibels or to log-compressed signals if not log-compressed.

When working with linear-scale power gain factors, total gain is the product of the individual gains, requiring multiplication between quantities. To calculate total gain, it may be cumbersome if portions reduce the total gain, thereby requiring division as well as multiplication. Multiplication implemented in digital form is typically inefficient and expensive when compared to other arithmetic operations such as adders.

Rather than multiplying numbers, their logarithms may be added together, and the antilogarithm of the sum taken to find the product if the two numbers were multiplied. Mathematically, $\log(A \times B) = \log A + \log B$. To divide one number into another, the logarithm of the divisor is subtracted from the logarithm of the dividend, $$\log\left(\frac{A}{B}\right) = \log A - \log B.$$

The calculations used to teach the invention are in decibels or log-compressed or log-scale signals for simplicity and efficiency. Alternatively, linear-scale power gain factors may be used, using the mathematical operations described above.

Gain variation $\Delta$'s between axial section representative signal values are calculated. To calculate gain variation $\Delta$'s, one section from the plurality of sections is selected as a reference position and a distribution direction is chosen. For gain variation calculations proceeding in the chosen distribution direction, a section representative signal value is subtracted from an adjacent section representative signal value further away from the reference position. For gain variation calculations not proceeding in the chosen distribution direction, a section representative signal value is subtracted from an adjacent section representative signal value nearer to the reference position. These calculations include the representative signal value for the reference position (step 335).

In conjunction with the gain variation $\Delta$'s, each axial section ASA, ASB, ASC, ASD and ASE representative signal value is compared with an adjacent axial section representative signal value, and compared with a predefined limit1 (step 340)

if $|\Delta_{ASB-ASA}| >$ limit 1, then substitute zero, or a predefined value  (6)

if $|\Delta_{ASC-ASB}| >$ limit 1, then substitute zero, or a predefined value if $|\Delta_{ASD-ASC}| >$ limit 1, then substitute zero, or a predefined value if $|\Delta_{ASE-ASD}| >$ limit 1, then substitute zero, or a predefined value.

If the absolute difference between one section representative signal value and its adjacent section representative signal value is greater than the predefined limit1, instead of using that gain variation $\Delta$ value ($\Delta_{ASB-ASA}$, $\Delta_{ASC-ASB}$, $\Delta_{ASD-ASC}$ and $\Delta_{ASE-ASD}$, or $\Delta_{ASD-ASE}$, $\Delta_{ASC-ASD}$, $\Delta_{ASB-ASC}$ and $\Delta_{ASB-ASA}$) zero, or a predefined value is substituted for that gain variation $\Delta$ value. The substitution prevents a gross skew in the distribution. In an alternative embodiment, the comparison and substitution process may not occur.

A number of gain variation distribution series values are calculated from the gain variation $\Delta$'s. The reference position section representative signal value is used as one of the distribution series values. A new distribution series value is calculated by adding a gain variation $\Delta$ to a previous gain variation distribution series value if in the distribution direction, or by subtracting a gain variation $\Delta$ from a previous gain variation distribution series value if not in the distribution direction. The entire series of distribution series values are arranged in order (step 345).

Using the shallowest axial section ASA as the reference position with a top to bottom distribution direction $$I_{ASA} = \text{axial gain var } dist1 \quad (7)$$

$$I_{ASA} + \Delta_{ASB-ASA} = \text{axial gain var } dist2$$

$$I_{ASA} + \Delta_{ASB-ASA} + \Delta_{ASC-ASB} = \text{axial gain var } dist3$$

$$I_{ASA} + \Delta_{ASB-ASA} + \Delta_{ASC-ASB} + \Delta_{ASD-ASC} = \text{axial gain var } dist4$$

$$I_{ASA} + \Delta_{ASB-ASA} + \Delta_{ASC-ASB} + \Delta_{ASD-ASC} + \Delta_{ASE-ASD} =$$
$$\text{axial gain var } dist5.$$

Using the deepest axial section ASE as the reference position with a bottom to top distribution direction $$I_{ASE} = \text{axial gain var } dist5 \qquad (8)$$

$$I_{ASE} + \Delta_{ASD-ASE} = \text{axial gain var } dist4$$

$$I_{ASE} + \Delta_{ASD-ASE} + \Delta_{ASC-ASD} = \text{axial gain var } dist3$$

$$I_{ASE} + \Delta_{ASD-ASE} + \Delta_{ASC-ASD} + \Delta_{ASB-ASC} = \text{axial gain var } dist2$$

$$I_{ASE} + \Delta_{ASD-ASE} + \Delta_{ASC-ASD} + \Delta_{ASB-ASC} + \Delta_{ASA-ASB} =$$
$$\text{axial gain var } dist1.$$

Using a middle axial section ASC as the reference position with a top to bottom distribution direction $$I_{ASC} - \Delta_{ASC-ASB} - \Delta_{ASB-ASA} = \text{axial gain var } dist1 \qquad (9)$$

$$I_{ASC} - \Delta_{ASC-ASB} = \text{axial gain var } dist2$$

$$I_{ASC} = \text{axial gain var } dist3$$

$$I_{ASC} + \Delta_{ASD-ASC} = \text{axial gain var } dist4$$

$$I_{ASC} + \Delta_{ASD-ASC} + \Delta_{ASE-ASD} = \text{axial gain var } dist5.$$

Figure 5:
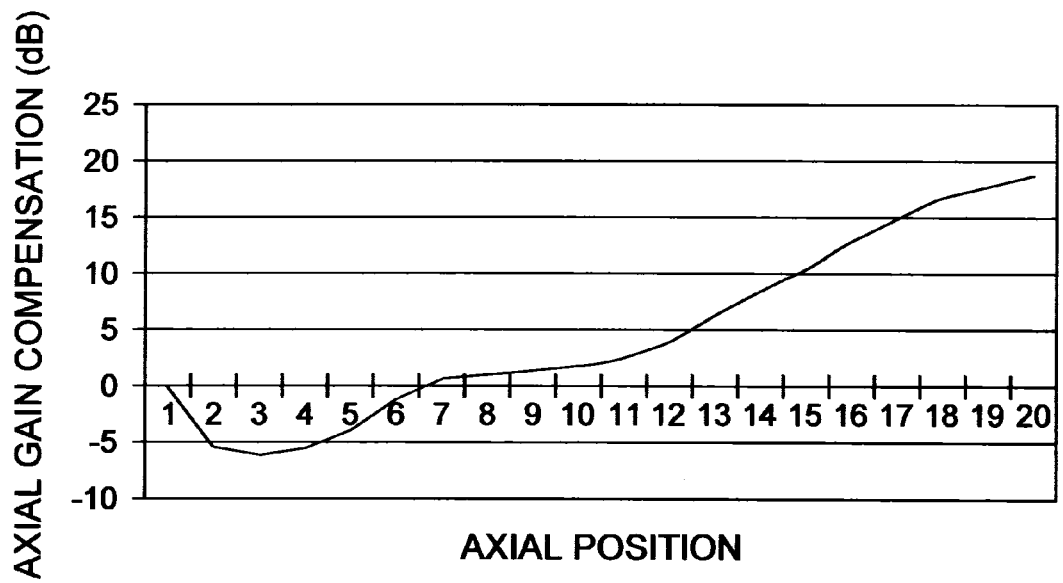
FIG. 5 is an exemplary axial gain compensation curve.

The entire series of distribution series values in order 1, 2, 3, 4 and 5 are assembled as a continuous gain variation curve (step 350) using interpolation functions such as linear, cubic-spline and others. An axial gain compensation curve is derived from the gain variation curve by changing the polarity (i.e., plus or minus) of the gain variation curve. If the values are in linear-scale, the gain compensation curve is the reciprocal of the gain variation curve (step 355). An exemplary axial gain compensation curve is shown in FIG. 5 from an image data frame axially partitioned into 20 sections.

An axial gain compensation curve is used to compensate arriving signals via the variable gain TGC amplifiers $119_y$ and the variable gain axial amplifier 133 using the gain compensation curve data output by the axial engine 155 and apportioned by the director 161. The amount of gain from the axial compensation curve in relation to a position (axial depth) may be apportioned. Rather than potentially overloading the gain of the variable gain TGC amplifiers $119_y$, the gain may be apportioned between the variable gain TGC amplifiers $119_y$ and the variable gain axial amplifier 133. The axial gain compensation may be applied to a next received image data frame (step 360).

Figure 6:
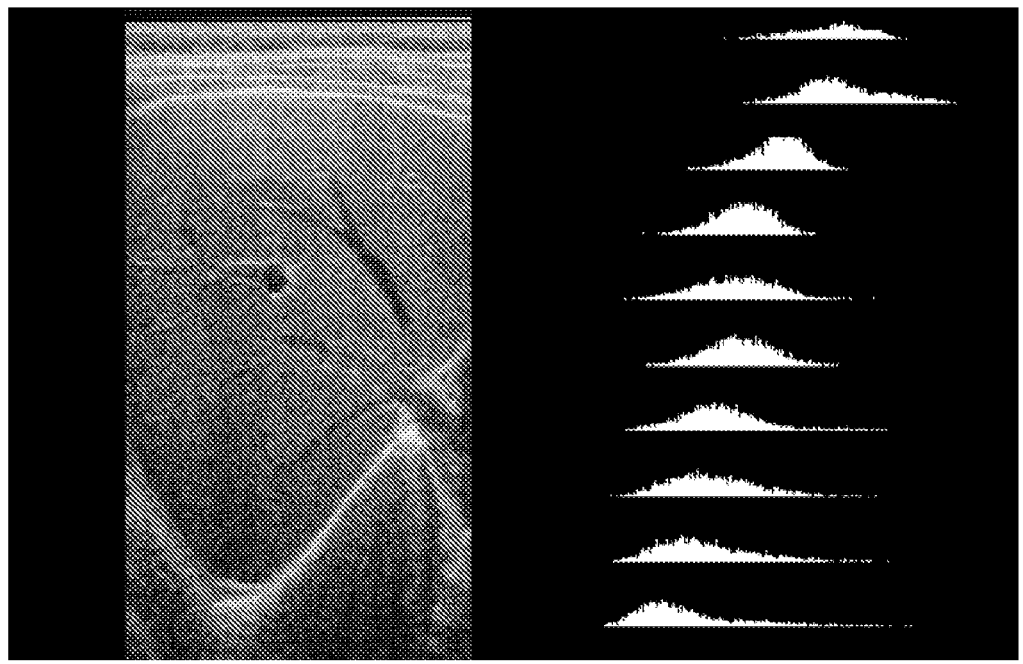
FIG. 6 is an ultrasound image before axial gain compensation with ten axial section histograms.
Figure 7:
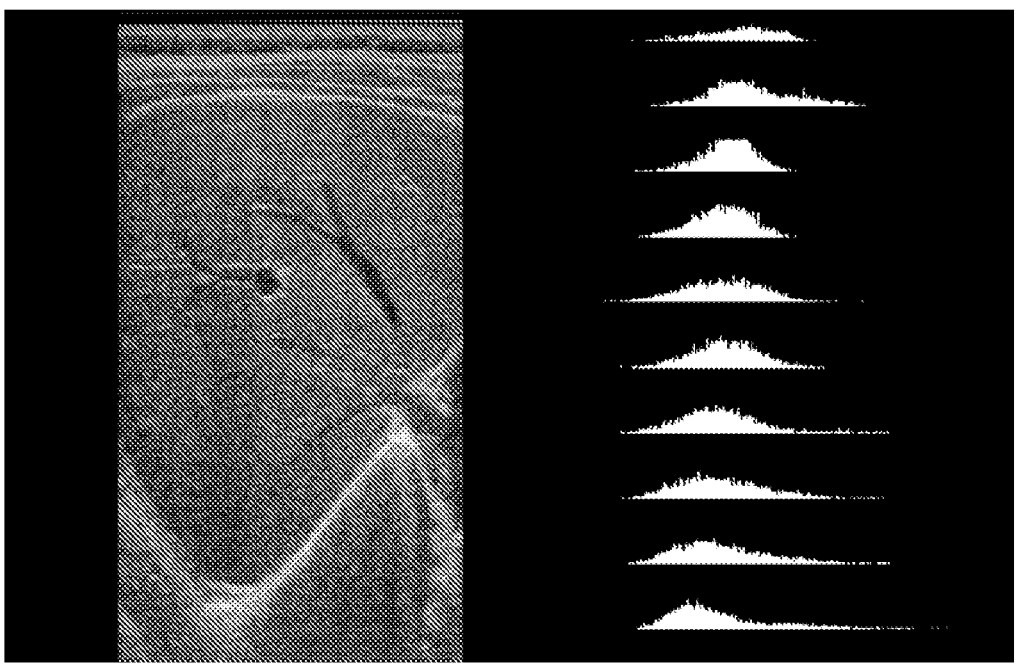
FIG. 7 is the ultrasound image shown in FIG. 6 after axial gain compensation with ten axial histograms showing a more uniform vertical intensity distribution

FIG. 6 shows an actual ultrasound image, partitioned into 10 axial sections. Shown alongside each section is its respective histogram. FIG. 7 shows the same ultrasound image after axial gain compensation. After axial gain compensation, the same sections were analyzed, with the resultant histograms shown. It can be seen that the image after compensation has a vertically uniform intensity. The histograms after compensation likewise show a uniform intensity distribution from section to section.

The same process is used to obtain a lateral gain compensation curve. To derive a lateral gain compensation curve, the image data frame is partitioned laterally. Shown in FIG. 8 is an exemplary lateral partitioning of the image frame shown in FIG. 2. For this example, the frame is partitioned into five equal lateral sections (LS) F, G, H, I, and J, each having three unique columns for a two-dimensional analysis (step 325). Each lateral section may contain up to 45 valid image data values $a_{i,j}$. However, as described above for axial analysis, the frame may be partitioned into any number of lateral sections, having any number of valid image data values $a_{i,j}$, and in a variety of shapes. Some sections may overlap with other sections sharing valid image data values.

The lateral engine 157 computes a representative signal value (I) for each defined lateral section LSF, LSG, LSH, LSI and LSJ using the valid image data values $a_{i,j}$ within each section. The representative signal values calculated for each lateral section are compared with adjacent lateral sections. The lateral section LSF, LSG, LSH, LSI and LSJ representative signal values may be converted to decibels if not in decibels or to log-compressed signals if not log-compressed before. The representative signal value computation may be performed using any of the above listed methods.

Gain variation $\Delta$'s between lateral section representative signal values are calculated based on a desired distribution direction (step 335).

In conjunction with the gain variation $\Delta$, each lateral section LSF, LSG, LSH, LSI and LSJ representative signal value is compared with an adjacent lateral section representative signal value and compared with a predefined limit2 (step 340)

$$\text{if } |\Delta_{LSF-LSG}| > \text{limit 2, then substitute zero, or a predefined value} \qquad (10)$$

$$\text{if } |\Delta_{LSG-LSH}| > \text{limit 2, then substitute zero, or a predefined value}$$

$$\text{if } |\Delta_{LSH-LSI}| > \text{limit 2, then substitute zero, or a predefined value}$$

$$\text{if } |\Delta_{LSI-LSJ}| > \text{limit 2, then substitute zero, or a predefined value.}$$

If the absolute difference between one section representative signal value and its adjacent section representative signal value is greater than the predefined limit2, instead of using that gain variation $\Delta$ value ($\Delta_{LSG-LSF}$, $\Delta_{LSH-LSG}$, $\Delta_{LSI-LSH}$ and $\Delta_{LSJ-LSI}$, or $\Delta_{LSI-LSJ}$, $\Delta_{LSH-LSI}$, $\Delta_{LSG-LSH}$ and $\Delta_{LSF-LSG}$), a zero, or a predefined value, is substituted for that gain variation $\Delta$ value. The substitution prevents a gross skew in the distribution. In an alternative embodiment, the comparison and substitution process may not be performed.

A gain variation distribution for lateral sections is a lateral accumulation series. The series continues until all lateral gain variation $\Delta$ values have been considered (step 345).

Using the right end lateral section LSF as the reference position with a right to left distribution direction $$I_{LSF} = \text{lat gain var } dist1 \qquad (11)$$

$$I_{LSF} + \Delta_{LSG-LSF} = \text{lat gain var } dist2$$

$$I_{LSF} + \Delta_{LSG-LSF} + \Delta_{LSH-LSG} = \text{lat gain var } dist3$$

$$I_{LSF} + \Delta_{LSG-LSF} + \Delta_{LSH-LSG} + \Delta_{LSI-LSH} = \text{lat gain var } dist4$$

$$I_{LSF} + \Delta_{LSG-LSF} + \Delta_{LSH-LSG} + \Delta_{LSI-LSH} + \Delta_{LSJ-LSI} =$$
$$\text{lat gain var } dist5.$$

Using the left end lateral section LSJ as the reference position with a left to right distribution direction $$I_{LSJ} = \text{lat gain var } dist5 \qquad (12)$$

$$I_{LSJ} + \Delta_{LSI-LSJ} = \text{lat gain var } dist4$$

$$I_{LSJ} + \Delta_{LSI-LSJ} + \Delta_{LSH-LSI} = \text{lat gain var } dist3$$

$$I_{LSJ} + \Delta_{LSI-LSJ} + \Delta_{LSH-LSI} + \Delta_{LSG-LSH} = \text{lat gain var } dist2$$

$$I_{LSJ} + \Delta_{LSI-LSJ} + \Delta_{LSH-LSI} + \Delta_{LSG-LSH} + \Delta_{LSF-LSG} =$$
$$\text{lat gain var } dist1.$$

Figure 9:
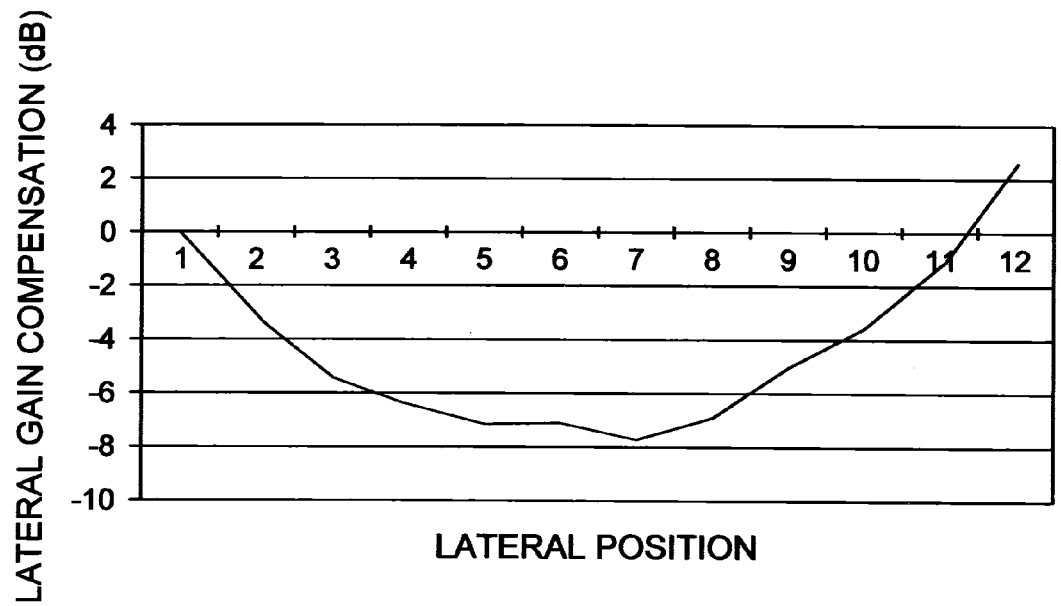
FIG. 9 is an exemplary lateral gain compensation curve.

The entire series of distribution series values in order 1, 2, 3, 4 and 5 are assembled as a continuous gain variation curve (step 350) using interpolation functions. A lateral gain compensation curve is derived from the gain variation curve by changing the polarity (i.e., plus or minus) of the gain variation curve. If the values are in linear-scale, the gain compensation curve is the reciprocal of the gain variation curve (step 355). An exemplary lateral gain compensation curve is shown in FIG. 9 from an image data frame laterally partitioned into 12 sections.

A lateral gain compensation curve is used to compensate arriving signals via the variable gain TGC amplifiers 119$_y$ and the variable gain lateral amplifier 135 using the lateral gain compensation curve data output by the lateral engine 157 and director 161. The amount of gain from the lateral compensation curve may be apportioned between the amplifiers. Using high speed TGC amplifiers, a lateral gain compensation curve may be applied to the TGC amplifiers for every received ultrasound signal, effecting lateral gain compensation. Typically, the variable gain lateral gain amplifier 135 is used to compensate for lateral gain variations. Rather than overloading the gain of the variable gain TGC amplifiers 119$y$, the gain may be apportioned between the variable gain TGC amplifiers 119$y$ and the variable gain lateral amplifier 135. The lateral compensation may be applied to one or more incoming image data frames (step 360).

Figure 10:
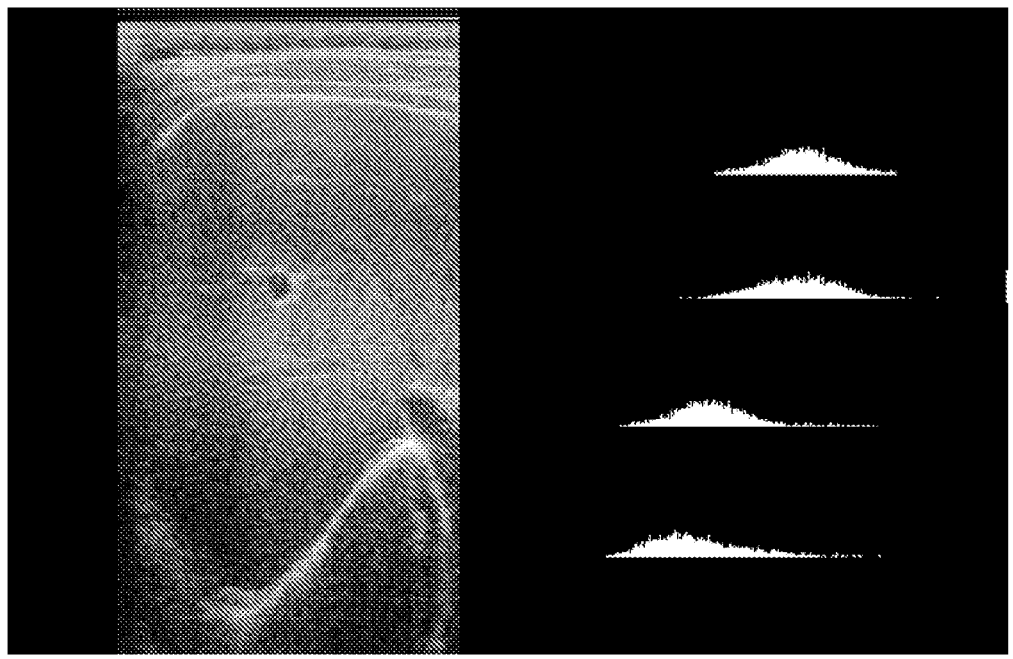
FIG. 10 is an ultrasound image before lateral gain compensation with four lateral section histograms.
Figure 11:
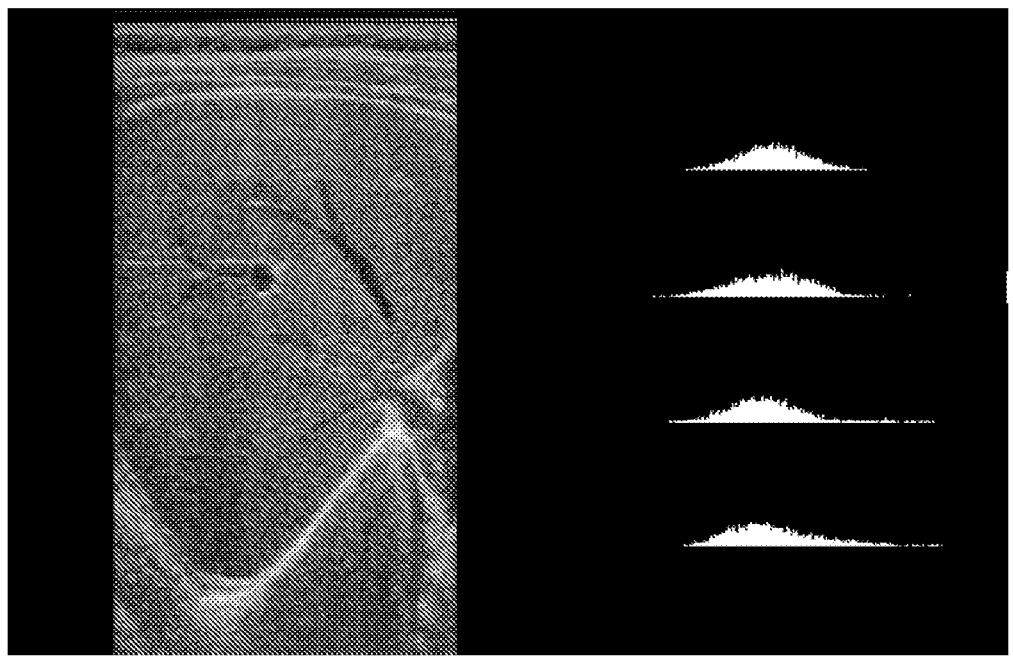
FIG. 11 is the ultrasound image shown in FIG. 10 after lateral gain compensation with four lateral histograms showing a more uniform horizontal intensity distribution.

FIG. 10 shows an actual ultrasound image partitioned into 4 lateral sections, with the resultant histograms for each respective section shown alongside. FIG. 11 shows the same ultrasound image after lateral gain compensation. After lateral gain compensation, the same sections were analyzed, with the resultant histograms shown. It can be seen that the image after processing has uniform horizontal intensity. The histograms likewise show a uniform intensity distribution from section to section.

Figure 12:
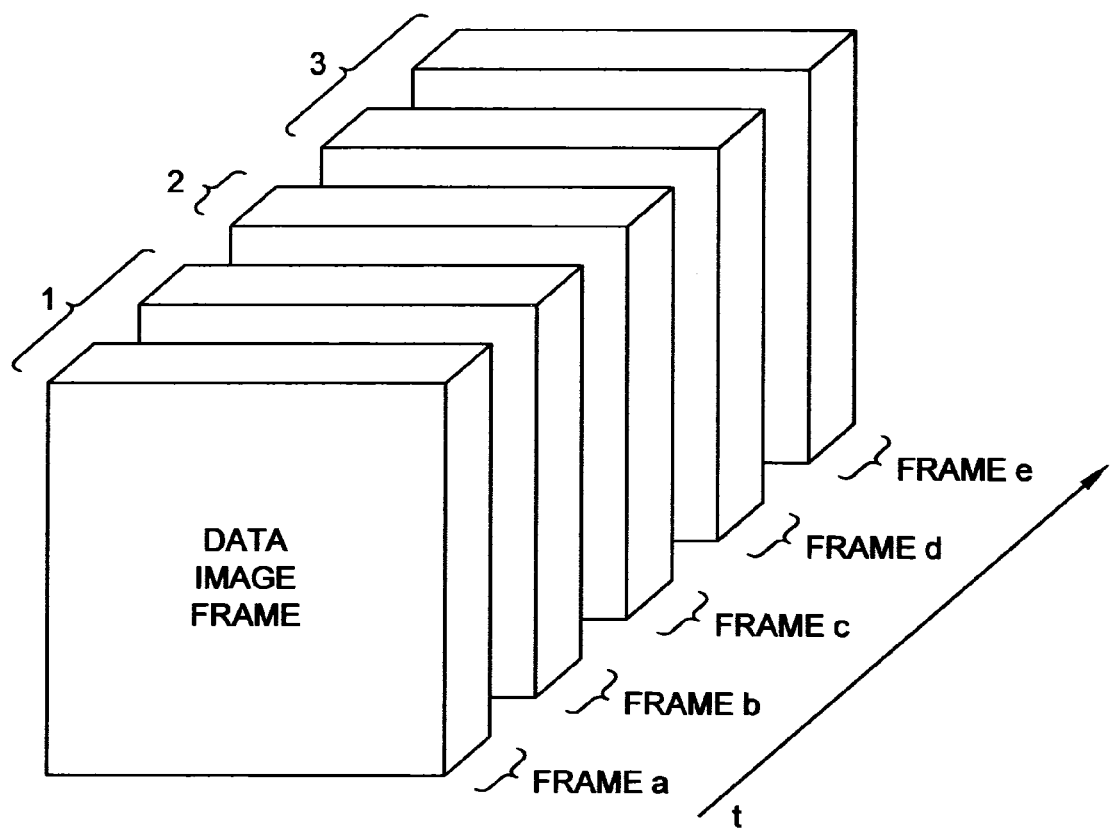
FIG. 12 is an exemplary elevation sectioning of a five image data frame volume.

Since the computation of an elevation gain compensation curve is used for volume imaging, a series of frames are required (steps 320, 365). Shown in FIG. 12 is an exemplary elevation calculation for a series of five consecutive ultrasound image frames a, b, c, d, and e. Typically, 50 to 100 frames or more may comprise a volume. Lower and upper limits $limit_{lower}$, $limit_{upper}$ are applied to each image data value $limit_{lower} < a_{i,j} < limit_{upper}$, $limit_{lower} < b_{i,j} < limit_{upper}$, $limit_{lower} < c_{i,j} < limit_{upper}$, $limit_{lower} < d_{i,j} < limit_{upper}$ and $limit_{lower} < e_{i,j} < limit_{upper}$ to determine valid frame image data values (step 315).

The elevation engine 159 computes a representative signal value (I) for each defined elevation section (ES) which may be an individual frame (ESa, ESb, ESc, ESd and ESe) or a group of frames (ES1=Framea+Frameb, ES2=Framec and ES3=Framed+Framee) (step 375). Frame groups lessen calculation expense when volumes comprising 50 to 100 frames are considered. The representative signal values calculated for each elevation section are compared with adjacent elevation section representative signal values. The elevation section representative signal values may be converted to decibels or log-compressed signals.

As in the previous sectioning methods, not all valid image data values are necessary. For example, a sampling across a frame, or a frame group may be performed, or a predefined pattern or shape capturing image data values in each frame or frame group may be used. Elevation sections may, or may not share valid image data values (overlap) with one another. The valid image data values in a defined elevation section are used. The representative signal value computation may be performed using any of the above listed methods.

Gain variation Δ's between adjacent elevation section representative signal values are calculated based on a desired distribution direction (step 380).

In conjunction with elevation gain variation Δ's, each elevation section representative signal value is compared with an adjacent elevation section representative signal value and compared with a predefined limit3 (step 385)

if $|\Delta_{ES1-ES2}|$ > limit 3, then substitute zero, or a predefined value (13)

if $|\Delta_{ES2-ES3}|$ > limit 3, then substitute zero, or a predefined value.

If the absolute difference between one elevation section representative signal value and its adjacent elevation section representative signal value is greater than the predefined limit3, instead of using that gain variation Δ value ($\Delta_{ES1-ES2}$ and $\Delta_{ES2-ES3}$, or $\Delta_{ES3-ES2}$ and $\Delta_{ES2-ES1}$), zero, or a predefined value is substituted for that gain variation Δ value. In an alternative embodiment, the comparison and substitution process may not be performed.

A gain variation distribution for elevation sections is an elevation accumulation series. The series continues until all elevation section gain variation Δ values have been considered (step 390).

Using the front elevation section ES1 as the reference position with a front to back distribution direction $$I_{ES1} = \text{elevation gain var } dist1 \quad (14)$$
$$I_{ES1} + \Delta_{ES2-ES1} = \text{elevation gain var } dist2$$
$$I_{ES1} + \Delta_{ES2-ES1} + \Delta_{ES3-ES2} = \text{elevation gain var } dist3.$$

Using the back elevation section ES3 as the reference position with a back to front distribution direction $$I_{ES3} = \text{elevation gain var } dist3 \quad (15)$$
$$I_{ES3} + \Delta_{ES2-ES3} = \text{elevation gain var } dist2$$
$$I_{ES3} + \Delta_{ES2-ES3} + \Delta_{ES1-ES2} = \text{elevation gain var } dist1$$

Figure 13:
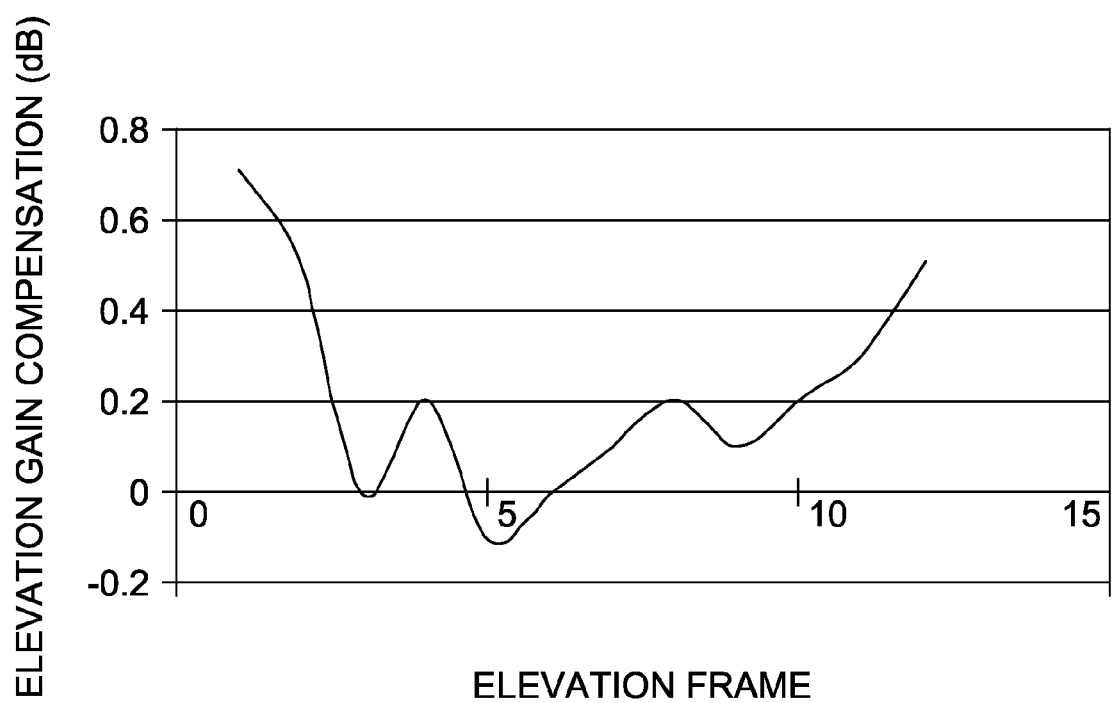
FIG. 13 is an exemplary elevation gain compensation curve.

The entire series of distribution series values in order 1, 2, and 3 are assembled as a continuous gain variation curve (step 395) using interpolation functions. An elevation gain compensation curve is derived from the gain variation curve by changing the polarity (i.e., plus of minus) of the gain variation curve. If the values are in linear-scale, the gain compensation curve is the reciprocal of the gain variation curve (step 397). An exemplary elevation compensation curve is shown in FIG. 13.

An elevation gain compensation curve is used to compensate arriving signals using the variable gain TGC amplifiers 119$y$ and variable gain elevation amplifier 143 using the elevation gain compensation curve data output by the elevation engine 159 and director 161. The elevation compensation may be applied to the next series of frames in a volume (step 360).

Shown in FIG. 14 is an exemplary axial sectioning of a five image frames. For axial volume gain compensation, the axial engine 155 computes a representative signal value for the same axial section throughout the volume (steps 365, 370).

An axial volume section (AVS) may be the same region of image data values in Frame a, throughout Frames b, c, d and e. The volume may be partitioned into any number of axial sections, with sections having the same or different number of image data values. As previously described, a sampling in the form of a cylinder, elliptical cylinder, or other shape may be used throughout the volume as a section. Additionally, some sections may overlap with other sections. The valid image data values in a defined section are used.

The axial engine 155 computes a representative signal value (I) for each defined axial volume section (step 370) AVSA, AVSB, AVSC, AVSD, and AVSE, which is compared with adjacent axial volume section representative signal values. The axial volume section AVSA, AVSB, AVSC, AVSD and AVSE representative signal values may be converted to decibels if not in decibels or to log-compressed signals. As above, the representative signal value analysis may be performed using several different methods.

Gain variation Δ's between adjacent axial volume sections are calculated based on a desired distribution direction (step 375).

In conjunction with the gain variation Δ, each axial volume section AVSA, AVSB, AVSC, AVSD and AVSE representative signal value is compared with an adjacent axial volume section representative signal value and compared with a predefined limit4 (step 385)

$$\text{if } |\Delta_{AVSA-AVSB}| > \text{limit 4}, \qquad (16)$$

then substitute zero, or a predefined value if $|\Delta_{AVSB-AVSC}| > \text{limit 4}$, then substitute zero, or a predefined value if $|\Delta_{AVSC-AVSD}| > \text{limit 4}$, then substitute zero, or a predefined value if $|\Delta_{AVSD-AVSE}| > \text{limit 4}$, then substitute zero, or a predefined value.

If the absolute difference between one axial volume section representative signal value and its adjacent axial volume section representative signal value is greater than the predefined limit4, instead of using that gain variation Δ value ($\Delta_{AVSB-AVSA}$, $\Delta_{AVSC-AVSB}$, $\Delta_{AVSD-AVSC}$ and $\Delta_{AVSE-AVSD}$, or $\Delta_{AVSA-AVSB}$, $\Delta_{AVSB-AVSC}$, $\Delta_{AVSC-AVSD}$, $\Delta_{AVSD-AVSE}$) zero, or a predefined value is substituted for that gain variation Δ value. The substitution prevents a gross skew in the distribution. In an alternative embodiment, the comparison and substitution process may not be performed.

A gain variation distribution for axial volume sections is an axial accumulation series. The series continues until all axial volume gain variation Δ values have been considered (step 390).

Using the shallowest axial volume section AVSA as the reference position with a top to bottom distribution direction $$I_{AVSA} = ax \text{ vol gain var } dist1 \qquad (17)$$

$I_{AVSA} + \Delta_{AVSB-AVSA} = ax \text{ vol gain var } dist2$ $I_{AVSA} + \Delta_{AVSB-AVSA} + \Delta_{AVSC-AVSB} = ax \text{ vol gain var } dist3$ $I_{AVSA} + \Delta_{AVSB-AVSA} + \Delta_{AVSC-AVSB} + \Delta_{AVSD-AVSC} =$ $ax \text{ vol gain var } dist4$ $I_{AVSA} + \Delta_{AVSB-AVSA} + \Delta_{AVSC-AVSB} + \Delta_{AVSD-AVSC} + \Delta_{AVSE-AVSD} =$ $ax \text{ vol gain var } dist5.$ Using the deepest axial volume section AVSE as the reference position with a bottom to top distribution direction $$I_{AVSE} = ax \text{ vol gain var } dist5 \qquad (18)$$

Figure 15:
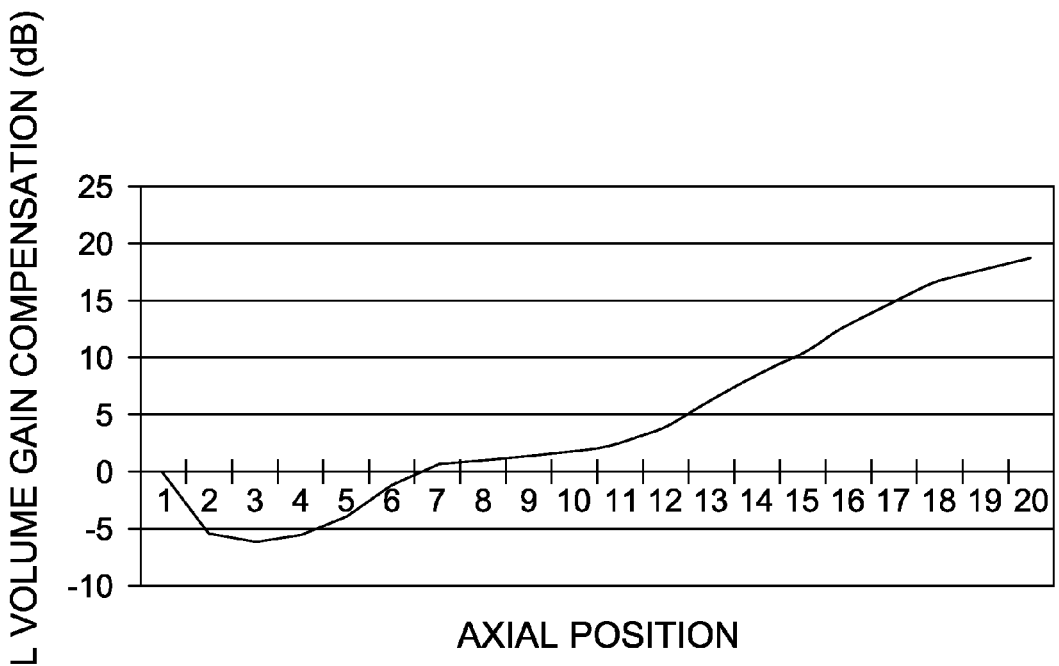
FIG. 15 is an exemplary axial volume gain compensation curve.

$I_{AVSE} + \Delta_{AVSD-AVSE} = ax \text{ vol gain var } dist4$ $I_{AVSE} + \Delta_{AVSD-AVSE} + \Delta_{AVSC-AVSD} = ax \text{ vol gain var } dist3$ $I_{AVSE} + \Delta_{AVSD-AVSE} + \Delta_{AVSC-AVSD} + \Delta_{AVSB-AVSC} =$ $ax \text{ vol gain var } dist2$ $I_{AVSE} + \Delta_{AVSD-AVSE} + \Delta_{AVSC-AVSD} + \Delta_{AVSB-AVSC} + \Delta_{AVSA-AVSD} =$ $ax \text{ vol gain var } dist1.$ The entire series of distribution series values in order 1, 2, 3, 4 and 5 are assembled as a continuous axial volume gain variation curve (step 395) using interpolation. An axial volume gain compensation curve is calculated from the axial volume gain variation curve by changing the polarity (i.e., plus or minus) of the axial volume gain variation (step 397). If the values are in linear-scale, the gain compensation curve is the reciprocal of the gain variation curve. An exemplary axial volume compensation curve is shown in FIG. 15.

An axial volume gain compensation curve is used to compensate arriving signals via the variable gain TGC amplifiers 119$_y$ and the variable gain axial amplifier 133 using the axial volume gain compensation curve data output by the axial engine 155 and apportioned by the director 161. The axial volume compensation may be applied to a next volume (step 360).

Figure 16:
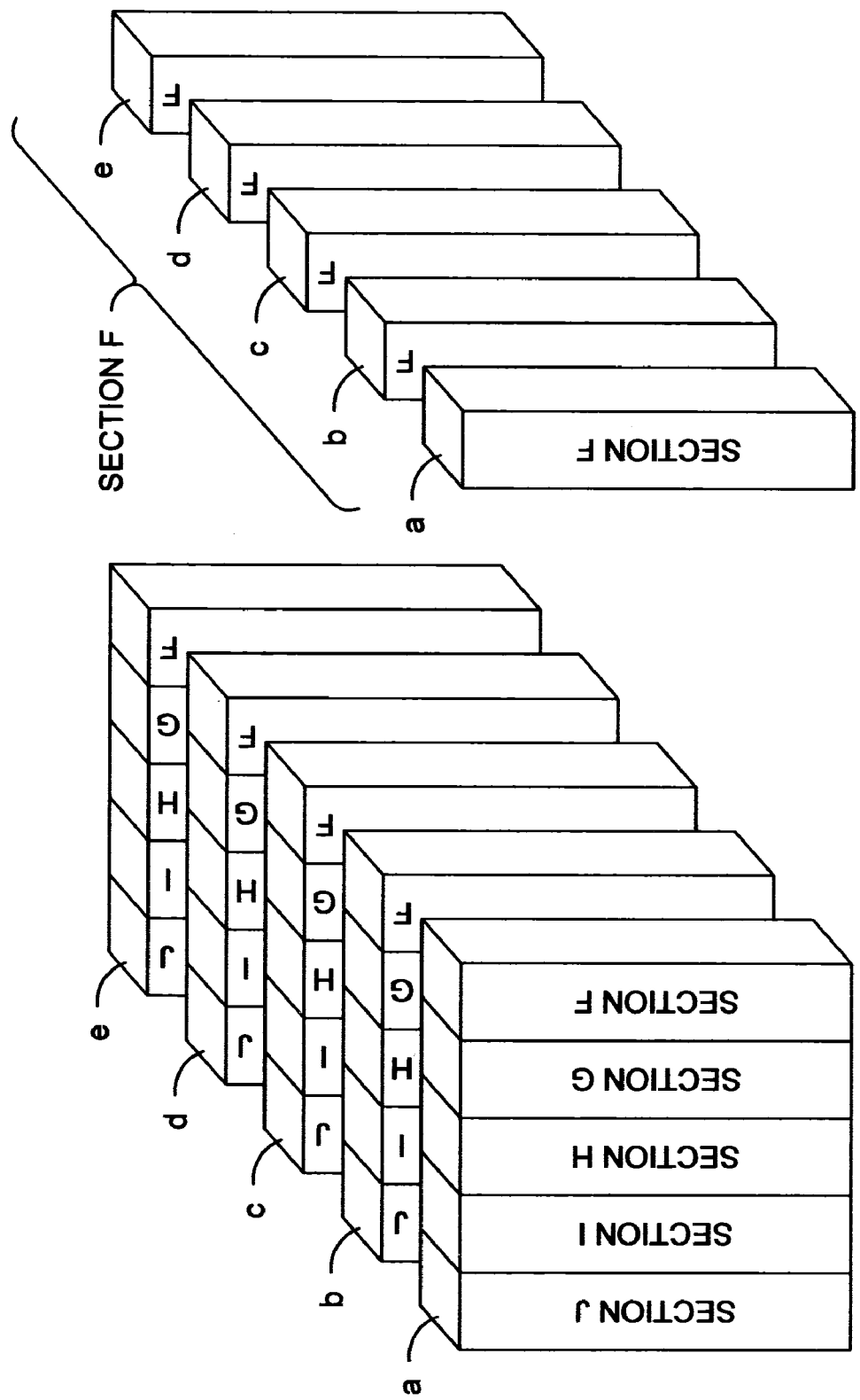
FIG. 16 is an exemplary lateral sectioning of a five image data frame volume.

Shown in FIG. 16 is an exemplary lateral volume sectioning of a five image data frame volume. For lateral volume gain compensation, the lateral engine 157 computes a representative signal value for the same lateral volume section throughout the volume (step 365).

A lateral volume section (LVS) may be the same region of image data values in Frame a, throughout Frames b, c, d and e. The volume may be partitioned into any number of lateral sections, with sections having the same or different number of image data values. As in the axial volume analysis, a sampling in the form of a cylinder, or other shape may be used throughout the volume as a section. Some sections may overlap with other sections. The valid image data values in a defined section are used.

The lateral engine 157 computes a representative signal value (I) for each defined lateral volume section LVSF, LVSG, LVSH, LVSI and LVSJ, which are then compared with adjacent lateral volume sections. The lateral volume section LVSF, LVSG, LVSH, LVSI and LVSJ representative signal values may be converted to decibels if not in decibels or to log-compressed signals. The representative signal value computation may be performed using any of the above listed methods.

Gain variation Δ's between adjacent lateral volume sections are calculated based on a desired direction (step 380).

In conjunction with the gain variation Δ, each lateral volume section LVSF, LVSG, LVSH, LVSI and LVSJ representative signal value is compared with an adjacent lateral volume section representative signal value and compared with a predefined limit5 (step 385)

if $|\Delta_{LVSF-LVSG}| >$ limit 5, then substitute zero, or a predefined value (19)

if $|\Delta_{LVSG-LVSH}| >$ limit 5, then substitute zero, or a predefined value if $|\Delta_{LVSH-LVSI}| >$ limit 5, then substitute zero, or a predefined value if $|\Delta_{LVSI-LVSJ}| >$ limit 5, then substitute zero, or a predefined value.

If the absolute difference between one lateral volume section representative signal value and its adjacent lateral volume section representative signal value is greater than the predefined limit5, instead of using that gain variation Δ value ($\Delta_{LVSF-LVSG}$, $\Delta_{LVSG-LVSH}$, $\Delta_{LVSH-LVSI}$ and $\Delta_{LVSI-LVSJ}$, or $\Delta_{LVSG-LVSF}$, $\Delta_{LVSH-LVSG}$, $\Delta_{LVSI-LVSH}$ and $\Delta_{LVSJ-LVSI}$), zero, or a predefined value is substituted for that gain variation Δ value. The substitution prevents a gross skew in the distribution. In an alternative embodiment, the comparison and substitution process may not be performed.

A gain variation distribution for lateral volume sections is a lateral accumulation series. The series continues until all lateral volume gain variation Δ values have been considered (step 397).

Using the right end lateral volume section LVSF as the reference position with a right to left distribution direction $$I_{LVSF} = lat\ vol\ \text{gain var } dist1 \quad (20)$$

$$I_{LVSF} + \Delta_{LVSG-LVSF} = lat\ vol\ \text{gain var } dist2$$

$$I_{LVSF} + \Delta_{LVSG-LVSF} + \Delta_{LVSH-LVSG} = lat\ vol\ \text{gain var } dist3$$

$$I_{LVSF} + \Delta_{LVSG-LVSF} + \Delta_{LVSH-LVSG} + \Delta_{LVSI-LVSH} = lat\ vol\ \text{gain var } dist4$$

$$I_{LVSF} + \Delta_{LVSG-LVSF} + \Delta_{LVSH-LVSG} + \Delta_{LVSI-LVSH} + \Delta_{LVSJ-LVSI} = lat\ vol\ \text{gain var } dist5.$$

Using the left end lateral volume section LVSJ as the reference position with a right to left distribution direction $$I_{LVSJ} = lat\ vol\ \text{gain var } dist5 \quad (21)$$

$$I_{LVSJ} + \Delta_{LVSI-LVSJ} = lat\ vol\ \text{gain var } dist4$$

$$I_{LVSJ} + \Delta_{LVSI-LVSJ} + \Delta_{LVSH-LVSI} = lat\ vol\ \text{gain var } dist3$$

$$I_{LVSJ} + \Delta_{LVSI-LVSJ} + \Delta_{LVSH-LVSI} + \Delta_{LVSG-LVSH} = lat\ vol\ \text{gain var } dist2$$

$$I_{LVSJ} + \Delta_{LVSI-LVSJ} + \Delta_{LVSH-LVSI} + \Delta_{LVSG-LVSH} + \Delta_{LVSF-LVSG} = lat\ vol\ \text{gain var } dist1.$$

Figure 17:
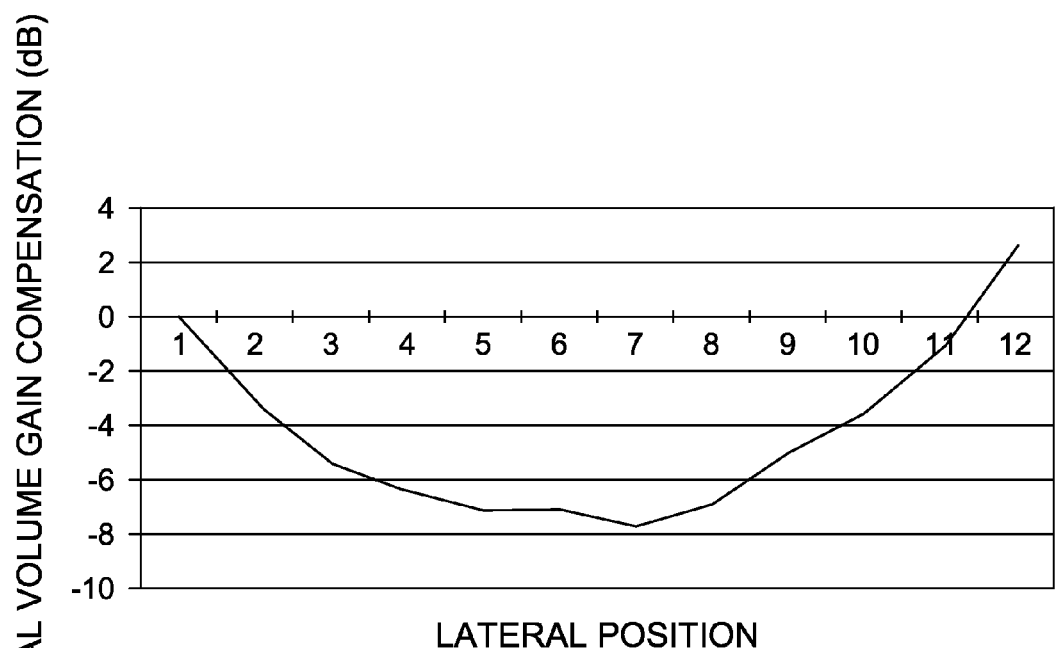
FIG. 17 is an exemplary lateral volume gain compensation curve.

The entire series of distribution series values in order 1, 2, 3, 4 and 5 are assembled as a continuous lateral volume gain variation curve (step 395) using interpolation functions. A lateral volume gain variation curve is derived from the gain variation curve by changing the polarity (i.e., plus or minus) of the gain variation curve. If the values are in linear-scale, the gain compensation curve is the reciprocal of the gain variation curve (step 397). An exemplary lateral volume gain variation compensation curve is shown in FIG. 17.

A lateral volume gain compensation curve is used to compensate arriving signals via the variable gain TGC amplifiers 119$_y$, and the variable gain lateral amplifier 135 using the lateral volume gain compensation curve data output by the lateral engine 157 and apportioned by the director 161. The lateral compensation may be applied to a next volume (step 355).

As in the case of two-dimensional axial and/or lateral gain compensation curves, a combination of elevation and axial and/or lateral volume partitioning results in three volume gain compensation curves. Each curve may be applied to a next volume.

Any combination of elevation, axial and lateral gain compensation may be applied to a next, incoming image frame(s). The newly calculated gain compensation curves indicate differences from previous amplifiers gain curves that provided outputs to control the gain of each amplifier 119$_y$, 133, 135, 143. The gain compensation curves derived modify pre-existing gain curves.

Returning to FIG. 1, the outputs from the axial 155, lateral 157 and elevation 159 engines are input to the director 161 where the gain compensation curves are processed.

Since new gain compensation curves update, or modify, previously calculated gain compensation curves, each director 161 axial, lateral and elevation input is coupled to a corresponding gain adder 169a, b, c. An output of each adder 169a, b, c is coupled to a corresponding delay 171a, b, c, which is coupled to a memory 170a, b, c. The memory 170a, b, c stores a previous gain compensation curve upon initialization and afterwards, an updated combination gain. The gain adder 169a, b, c outputs a gain which is a combination of a newly calculated gain compensation curve and a previous or updated gain.

The axial delay 171a is used to delay the total TGC+axial amplifier gain curve (i.e. a combination of TGC and axial amplifier gains and is referred to as axial combination gain) by one frame such that the axial combination gain curve of the previous frame is stored in the memory 170a which is added to a new axial compensating curve to obtain a new axial combination gain curve.

Similarly, the lateral delay 171b is used to delay the total TGC+lateral amplifier gain curve (i.e. combination of TGC and lateral amplifier gains and is referred to as lateral combination gain) by one frame such that the lateral combination gain curve of the previous frame is stored in the memory 170b which is added to a new lateral compensating curve to obtain a new lateral combination gain curve.

The elevation delay 171c is used to delay the total TGC+elevation amplifier gain curve (i.e. combination of TGC and elevation amplifier gains and is referred to as elevation combination gain) by one volume such that the lateral combination gain curve of the previous volume is stored in the memory 170c which is added to the new elevation compensating curve to obtain a new elevation combination gain curve.

The outputs of the gain adders 169a, b, c are coupled to first 173a, b, c and second 175a, b, c weight multipliers. The first 173a, b, c weight multipliers are coupled to apportioning weights α (axial), β (lateral) and γ (elevation) and the second weight multipliers 175a, b, c are coupled to apportioning weights 1-α 177a, 1-β 177b, and 1-γ 177c.

The weights α, β, and γ determine how much of a respective gain compensation value at a time t is apportioned between a respective axial 133, lateral 135 and elevation 143 variable gain amplifier, and the variable gain section of the TGC amplifiers 119$_y$. The weights α, β, and γ are derived using an apportioning processor 179 which optimizes each weight α, β, and γ. A discussion of the optimization process that determines the weights α, β, and γ is beyond the scope of this disclosure.

The outputs from the second weight multipliers 175*a, b, c* are output to corresponding axial 133, lateral 135 and elevation 143 variable gain amplifiers.

The output from the axial weight multiplier 173*a* is coupled to an adder 179 and mean calculator 181. The mean calculator 181 obtains the mean of the output from the axial multiplier 173*a* which is subtracted from the axial weight multiplier 173*a* output and is coupled to a common adder 183. The adder 179 subtracts the TGC gain curve mean from the TGC gain curve so that a constant gain is applied to the TGC amplifiers 119$_y$ fixed gain section, and only a curve gain is applied to the TGC amplifiers 119*y* variable gain section. This operation conserves the dynamic range of the TGC amplifier. In an alternate embodiment, the mean and subtraction may not be used.

The axial combination gain curve is multiplied by α so that a portion of the gain curve is applied to the TGC amplifiers 119$_y$ variable gain section. The output of the adder 179 is coupled to a DAC (digital to analog converter) 185, if required, and output to the TGC amplifiers 119$_y$ variable gain section.

The lateral combination gain from memory 170*b* is updated every beam to achieve the effects of the lateral gain curve and is multiplied by β so that a part of the gain curve is applied to the TGC amplifier 119$_y$ variable gain. A lateral delay 187 is used to synchronize all gain curves.

The elevation combination gain from memory 170*c* is updated every frame to achieve the effects of the elevation gain curve and is multiplied by γ so that a part of the gain curve is applied to the TGC amplifiers 119$_y$ variable gain. An elevation delay 189 is used to synchronize all gain curves.

The outputs of the delays 187, 189 and the output of the mean calculator 181 are coupled to the common adder 183. The adder 183 combines all TGC amplifier 119$_y$ fixed gain portions. The combined gain is output to another adder 191 and combined with an overall gain output by a gain calculator 193.

The outputs of lateral 135 or elevation 143 amplifiers, for the case of three dimension imaging, is coupled to the overall gain calculator 193 to obtain the overall gain using a histogram, percentile, mean, mode, median. The overall gain in dB or log-scale is changed in polarity (minus or plus) and added a preset value to set the final image brightness to the preset value. This operation sets the overall image brightness to a preset brightness value that most users prefer.

The combined output from the adder 191 is the TGC amplifier 119$_y$ fixed gain portion. The TGC amplifier 119$_y$ fixed gain portion is coupled to the fixed, or programmable gain amplifier in a TGC amplifier 119$_y$ chip.

The axial, lateral and elevation gain variations are compensated for by the above operations, and the overall image gain is set to the preset image brightness a user may prefer. The invention provides uniformity across all image dimensions.

One or more embodiments of the present invention have been described. Nevertheless, it will be understood that various modifications may be made without departing from the spirit and scope of the invention. Accordingly, other embodiments are within the scope of the following claims.

What is claimed is:

1. A method for automatically deriving gain compensating data from ultrasound image data comprising:
   receiving ultrasound image data corresponding to an image scan, wherein the ultrasound image data is based on ultrasound signals attenuated by tissue;
   assembling an image frame from the ultrasound image data, the image frame having columns and rows of image data values where columns represent lateral position and rows represent axial position;
   partitioning the image data frame into a plurality of sections including associated image data values;
   for each of the plurality of sections, calculating a representative signal value based on the image data values associated with the section;
   calculating a gain variation between representative signal values of each pair of adjacent sections by:
   choosing one of the plurality of sections as a reference section;
   choosing a distribution direction from a position of the reference section to perform gain variation calculations;
   for each of the plurality of sections, for gain variation calculations proceeding in the distribution direction, subtracting a representative signal value of a section from a representative signal value of an adjacent section, a distance from the adjacent section to the reference section being greater than a distance from the section to the reference section; and
   for each of the plurality of sections, for gain variation calculations not proceeding in the distribution direction, subtracting a representative signal value of a section from a representative signal value of an adjacent section, a distance from the adjacent section to the reference section being less than a distance from the section to the reference section;
   calculating gain variation distribution series values from the calculated gain variations based on the distribution direction;
   calculating a gain variation curve from the gain variation distribution series values; and
   calculating a gain compensation curve from the gain variation curve,
   wherein a value of the gain compensation curve corresponds with a position.

2. The method according to claim 1 further comprising:
   examining each image data value in the frame for values outside of a lower and upper limit; and
   flagging the image data values outside the predefined lower and upper limits for non-use.

3. The method according to claim 2 wherein the ultrasound imaging data comprises RF data, IF data, baseband signal data, or line data.

4. The method according to claim 3 wherein the representative signal value for each section is calculated using histograms, percentile value, mean, median and mode.

5. The method according to claim 4 wherein each section includes the same number of image data values, a different number of image data values, or image data values shared with an adjacent section.

6. The method according to claim 1 wherein calculating the gain variation between representative signal values of each pair of adjacent sections further comprises:
   for gain variation calculations proceeding in the distribution direction, subtracting the representative signal value of the reference section from the representative signal value of the adjacent section if the adjacent section is next to the reference section; and
   for gain variation calculations not proceeding in the distribution direction, subtracting the representative signal value of the section from the representative signal value of the reference section if the adjacent section is next to the reference section.

7. The method according to claim 6 wherein calculating the gain variation distribution series values comprises:
   using the representative signal value of the reference section as one gain variation distribution series value; and
   creating a new gain variation distribution series value by adding a gain variation to a previous gain variation distribution series value if in the distribution direction, or by subtracting a gain variation from a previous gain variation distribution series value if not in the distribution direction.

8. The method according to claim 7 wherein the gain variation curve is calculated by a curve fit or interpolation of the gain variation distribution series values in order.

9. The method according to claim 8 wherein a gain compensation curve is calculated by changing the polarity of the gain variation curve.

10. The method according to claim 6 further comprising comparing an absolute value of each gain variation value with a predetermined limit wherein if an absolute gain variation value is greater than the predetermined limit, substituting a zero for that gain variation value.

11. The method according to claim 6 further comprising comparing an absolute value of each gain variation values with a predetermined limit wherein if an absolute gain variation value is greater than the predetermined limit, substituting a predetermined value for that gain variation value.

12. The method according to claim 6 wherein the plurality of sections are axial sections.

13. The method according to claim 6 wherein the plurality of sections are lateral sections.

14. A method for automatically deriving gain compensating data for an ultrasound image volume comprising:
   receiving ultrasound image data corresponding to a plurality of consecutive image scans, wherein the ultrasound image data is based on ultrasound signals attenuated by tissue;
   assembling an image volume from the plurality of image scans, the image volume having three dimensions of image data values where columns represent lateral position, rows represent axial position, and frames represent elevation position;
   partitioning the volume into a plurality of volume sections including associated image data values;
   for each of the plurality of volume sections, calculating a representative signal value based on the image data values associated with the volume section;
   calculating a gain variation between representative signal values of each pair of adjacent volume sections by:
   choosing one of the plurality of volume sections as a reference volume section;
   choosing a distribution direction from a position of the reference volume section to perform gain variation calculations;
   for each of the plurality of volume sections, for gain variation calculations proceeding in the distribution direction, subtracting a representative signal value of a volume section from a representative signal value of an adjacent volume section, distance from the adjacent volume section to the reference volume section being greater than a distance from the volume section to the reference volume section; and
   for each of the plurality of volume sections, for gain variation calculations not proceeding in the distribution direction, subtracting a representative signal value of a volume section from a representative signal value of an adjacent volume section, a distance from the adjacent volume section to the reference volume section being less than a distance from the volume section to the reference volume section;
   calculating gain variation distribution series values from the calculated gain variations based on the distribution direction;
   calculating a gain variation curve from the gain variation distribution series values; and
   calculating a gain compensation curve from the gain variation curve,
   wherein a value of the gain compensation curve corresponds with a position.

15. The method according to claim 14 further comprising:
   examining each image data value in the volume image for values outside of a predefined lower and upper limit; and
   flagging the image data values outside the lower and upper limits for non-use.

16. The method according to claim 15 wherein the ultrasound imaging data comprises RF data, IF data, baseband signal data, line data or image data.

17. The method according to claim 16 wherein the representative signal value for each volume section is calculated using histograms, percentile value, mean, median and mode.

18. The method according to claim 17 wherein each volume section includes the same number of image data values, a different number of image data values, or image data values shared with an adjacent volume section.

19. The method according to claim 14 wherein calculating the gain variation between representative signal values of each pair of adjacent volume sections further comprises:
   for gain variation calculations proceeding in the distribution direction, subtracting the representative signal value of the reference volume section from the representative signal value of the adjacent volume section if the adjacent volume section is next to the reference volume section; and
   for gain variation calculations not proceeding in the distribution direction, subtracting the representative signal value of the volume section from the representative signal value of the reference volume section if the adjacent volume section is next to the reference volume section.

20. The method according to claim 19 wherein calculating the gain variation distribution series values comprises:
   using the representative signal value of the reference volume section as one gain variation distribution series value; and
   creating a new gain variation distribution series value by adding a gain variation to a previous gain variation distribution series value if in the distribution direction, or by subtracting a gain variation from a previous gain variation distribution series value if not in the distribution direction.

21. The method according to claim 20 wherein the gain variation curve is calculated by a curve fit of the gain variation distribution series values in order.

22. The method according to claim 21 wherein a gain compensation curve is calculated by changing the polarity of the gain variation curve.

23. The method according to claim 19 further comprising comparing an absolute value of each gain variation value with a predetermined limit wherein if an absolute gain variation value is greater than the predetermined limit, substituting a zero for that gain variation value.

24. The method according to claim 19 further comprising comparing an absolute value of each gain variation values with a predetermined limit wherein if an absolute gain variation value is greater than the predetermined limit, substituting a predetermined value for that gain variation value.

25. The method according to claim 19 wherein the plurality of volume sections are elevation volume sections.

26. The method according to claim 19 wherein the plurality of volume sections are axial volume sections.

27. The method according to claim 19 wherein the plurality of volume sections are lateral volume sections.

28. An automatic gain compensation system for deriving gain compensating data for ultrasound systems having amplifiers configured to adjust a received signal's gain while acquiring ultrasound image data, the automatic gain compensation system comprising:
   an automatic gain processor configured for:
   receiving ultrasound image data corresponding to an image scan, wherein the ultrasound image data is based on ultrasound signals attenuated by tissue;
   assembling an image frame from the ultrasound image data, the image frame having columns and rows of image data values where columns represent lateral position and rows represent axial position;
   partitioning the image data frame into a plurality of sections including associated image data values;
   for each of the plurality of sections, calculating a representative signal value based on the image data values associated with the section;
   calculating a gain variation between representative signal values of each pair of adjacent sections by:
   choosing one of the plurality of sections as a reference section;
   choosing a distribution direction from a position of the reference section to perform gain variation calculations;
   for each of the plurality of sections, for gain variation calculations proceeding in the distribution direction, subtracting a representative signal value of a section from a representative signal value of an adjacent section, a distance from the adjacent section to the reference section being greater than a distance from the section to the reference section; and
   for each of the plurality of sections, for gain variation calculations not proceeding in the distribution direction, subtracting a representative signal value of a section from a representative signal value of an adjacent section, a distance from the adjacent section to the reference section being less than a distance from the section to the reference section;
   calculating gain variation distribution series values from the calculated gain variations based on the distribution direction;
   calculating a gain variation curve from the gain variation distribution series values; and
   calculating a gain compensation curve from the gain variation curve, wherein a value of the gain compensation curve corresponds with a position.

29. An automatic gain compensation system for deriving gain compensating data for ultrasound systems having amplifiers configured to adjust a received signal's gain while acquiring ultrasound image data, the automatic gain compensation system comprising:
   an automatic gain processor configured for:
   receiving ultrasound image data corresponding to a plurality of consecutive image scans, wherein the ultrasound image data is based on ultrasound signals attenuated by tissue;
   assembling an image volume from the plurality of image scans, the image volume having three dimensions of image data values where columns represent lateral position, rows represent axial position, and frames represent elevation position;
   partitioning the volume into a plurality of volume sections including associated image data values;
   for each of the plurality of volume sections, calculating a representative signal value based on the image data values associated with the volume section;
   calculating a gain variation between representative signal values of each pair of adjacent volume sections by:
   choosing one of the plurality of volume sections as a reference volume section;
   choosing a distribution direction from a position of the reference section to perform gain variation calculations;
   for each of the plurality of volume sections, for gain variation calculations proceeding in the distribution direction, subtracting a representative signal value of a volume section from a representative signal value of an adjacent volume section, distance from the adjacent volume section from the reference volume section being greater than a distance from the volume section to the reference volume section; and
   for each of the plurality of volume sections, for gain variation calculations not proceeding in the distribution direction, subtracting a representative signal value of a volume section from a representative signal value of an adjacent volume section a distance from the adjacent volume section to the reference volume section being less than a distance from the volume section to the reference volume section;
   calculating gain variation distribution series values from the calculated gain variations based on the distribution direction;
   calculating a gain variation curve from the gain variation distribution series values; and
   calculating a gain compensation curve from the gain variation curve,
   wherein a value of the gain compensation curve corresponds with a position.

* * * * *